(12) United States Patent
Bowen et al.

(10) Patent No.: US 6,369,078 B1
(45) Date of Patent: Apr. 9, 2002

(54) SOLENOPSIN DERIVATIVES AND ANALOGUES AS FIRE ANT SUPPRESSANTS

(76) Inventors: J. Phillip Bowen, P.O. Box 240, Hull, GA (US) 30646; M. Scott Furness, 7807 Yankee Harbor Dr., Montgomery Village, MD (US) 20886; David Whitmire, P.O. Box 393, Watkinsville, GA (US) 30677

(*) Notice: Subject to any disclaimer, the term of this patent is extended or adjusted under 35 U.S.C. 154(b) by 0 days.

(21) Appl. No.: 09/650,257

(22) Filed: Aug. 29, 2000

Related U.S. Application Data
(60) Provisional application No. 60/151,724, filed on Aug. 31, 1999.

(51) Int. Cl.[7] ............................................. A61K 31/445
(52) U.S. Cl. ........................ 514/315; 514/317; 546/184; 546/248
(58) Field of Search ................................ 514/315, 317; 546/184, 248

(56) References Cited

U.S. PATENT DOCUMENTS

| | | | |
|---|---|---|---|
| 4,874,611 A | 10/1989 | Wilson et al. | 424/410 |
| 4,910,209 A | 3/1990 | Rehmert, Jr. | 514/315 |
| 4,921,969 A | 5/1990 | Vander Meer et al. | 424/84 |
| 4,983,390 A | 1/1991 | Levy | 424/404 |
| 5,075,320 A | 12/1991 | Rehmert, Jr. | 514/315 |
| 5,098,914 A | 3/1992 | Rehmert, Jr. | 514/315 |
| 5,484,599 A | 1/1996 | Yoder et al. | 424/405 |
| 5,571,522 A | 11/1996 | Munson et al. | 424/410 |
| 5,690,951 A | 11/1997 | Lew et al. | 424/410 |
| 5,837,273 A | 11/1998 | Shasha et al. | 424/405 |
| 5,850,707 A | 12/1998 | Fell et al. | 43/131 |
| 5,897,859 A | 4/1999 | Vander Meer et al. | 424/84 |
| 5,900,243 A | 5/1999 | Yoder et al. | 424/405 |
| 6,153,624 A | * 11/2000 | Alanine et al. | 514/317 |

OTHER PUBLICATIONS

Holland "2–sibstituted–5–sulfamoylbenzoic acids for treating vascular diseases" CA 77:48046 (1972).*
Blum "Alkoidal venom mace:offensive use by a thief ant" CA 92:212121 (1980).*
Carruthers et al. "Synthesis of trans–2,6–dialkylpiperidines by intramolecular . . . " CA 102:131883 (1984).*
Obin et al. "Gaster flagging by fire ants" CA 104:66314 (1985).*

* cited by examiner

*Primary Examiner*—Ceila Chang
(74) *Attorney, Agent, or Firm*—H. Coleman; R. N. Sudol; W. J. Sapone

(57) ABSTRACT

The present invention relates to solenopsin alkaloid derivatives which are trans-2,6-disubstituted piperidines according to the structure:

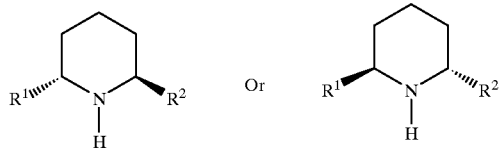

wherein $R^1$ and $R^2$ are selected from a $C_1$ to $C_{20}$ saturated or unsaturated linear, cyclic or branch-chained substituted or unsubstituted hydrocarbon group or a substituted or unsubstituted aromatic group, or an ester group. In certain preferred embodiments, where $R^1$ or $R^2$ contains an unsaturated group, such as an alkenyl group, the double bond in the alkenyl group preferably is found in the hydrocarbon chain between the carbon atom bonded to the piperidine ring and the adjacent carbon atom ($\alpha$ and $\beta$ carbons).

20 Claims, 4 Drawing Sheets

$R^1$ or $R^2$ =

SCHEME I

SCHEME II

SOLENOPSIN DERIVATIVES AND ANALOGUES AS FIRE ANT SUPPRESSANTS

RELATED APPLICATIONS

This application derives priority from provisional application Ser. No. 60/151,724, filed Aug. 31, 1999 of the same title.

FIELD OF THE INVENTION

This invention relates to novel analogues of solenopsin and their use as inhibitors of the biosynthesis of the venom of fire ants, repellents and/or insecticides.

BACKGROUND OF THE INVENTION

The solenopsins are piperidine alkaloids derived from the venom of the red fire ant *Solenopsis invicta*. The venom of this insect consists of 95% alkaloids and the remainder contains solubilized proteins, amino acids and enzymes including hyaluronidase and phospholipase. Among the piperidine alkaloids, the two major components are Solenopsin A, a trans-2-methyl 6-n-undecylpiperidine and Solenopsin B, a 2,6-trans-dialkyl-piperidine. Additionally, Solenopsin A, the primary component and Solenopsin B can be produced synthetically.

The red imported fire ants *Solenopsis invicta* were accidentally introduced into the southeastern United States around 1929, and they currently infest more than 290 million acres of land in eleven states and Puerto Rico. They are considered to be pests because of their painful stings, to which some people are allergic, and because of their deleterious effects on biodiversity and agriculture.

Fire ants are native species of South America, found naturally in southern Brazil, northern Argentina, and throughout Uruguay. Buren, et al., *Zoogeography of the imported fire ants. N.Y. Entomol. Soc.* 1974, 82, 113–124. Their natural habitat is one of constant environmental upheaval resulting from the flooding of the Paraguay river. As a result, fire ants have evolved mechanisms over time to quickly recover from environmental turbulence and repopulate the disturbed environment of the flood plain. Mann, C. C. *Science*, 1994, 18, 18–19. Upon introduction into North America, this adaptive ability of fire ants was instrumental in the spread of the species throughout the southeast. Jemal, A.; Jones, M. H. *Preventive Veterinary Medicine*, 1993, 17, 19–32.

*S. invicta* prefer open habitats such as pastures and lawns, but they have been shown to naturally occupy woodland areas also. Jemal, A.; Jones, M. H. *Preventive Veterinary Medicine*, 1993, 17, 19–32. Tschinkel and coworkers coined the description "weed species" for red imported fire ants (RIFA), which refers to the ants ability to opportunistically invade disturbed environments. Tschinkel, W. R. *Fire ants and Leaf-cutting ants: Biology and Management*. Eds. Clifford Logren and Rober Vander Meer. 1986, Westview Press, 72–87. Not surprisingly, human progress has provided an abundance of disturbed environments as a result of general urbanization. There is considerable evidence that RIFA are susceptible to very dry and hot environmental conditions. Moreover, since *S. invicta* cannot survive temperatures below freezing, climate conditions have limited their northward expansion into North America.

A typical RIFA colony has a shallow but extensive network of tunnels. Although the tunnels range in depth from only 2–12 meters, they can radiate from the mound to a distance of over 25 feet. The mounds have been shown to maintain temperature and humidity, even in water saturated soil conditions. Shower, A. T.; Reagan, T. E. *J. Entomol. Sci. Suppl.* 1987, 1, 52–64.

Fire ants typically sting their prey to defend their mounds from larger animals. Any disturbance sends hundreds of workers out to assault anything that moves. The fire ant grabs onto its victim with its jaws, and then inserts its stinger. Once the ant attaches in this manner, it can sting several times without letting go. Moreover, stinging releases chemical messengers which provokes other ants into the same process.

The venom fire ants secrete contains mostly alkaloids and a small amount of protein. Once stung, the victim experiences a sharp pain for a few minutes. The sting then starts to itch, and a welt appears. The alkaloid kills skin cells, and the proteins can elicit allergic responses such as nausea, vomiting, dizziness, and asthma which require medical attention. There have been cases of death where adults have extreme allergic reactions, and where toddlers have fallen on the fire ant mounds. Deshazo, R. D.; Butcher, B. T., Banks, W. A. *N. Engl. J. Med.* 1990, 323, 462–466.

*S. invicta* have been known to destroy other insect species, crops, and even farm machinery. MacKay, W. P.; Vinson, S. B. *Applied Myrmecology: A World Perspective*. Eds. Robert Vander Meer, Klaus Jaffe, Aragua Cedeno. 1990, Westview Press, Boulder, 614–619. Although they eat a wide variety of foods, fire ants primarily eat other invertebrates such as spiders, scorpions, mites, centipedes, and earthworms. Tschinkel, W. R. *Fire ants and Leaf-cutting ants: Biology and Management*. Eds. Clifford Logren and Rober Vander Meer. 1986, Westview Press, 72–87. Their presence can even reduce or eliminate ground-nesting mammals and birds. Jemal, A.; Jones, M. H. *Preventive Veterinary Medicine*, 1993, 17, 19–32. Fire ants have had significant deleterious effects on crop yields of soybeans, corn, potatoes, okra, and berries by feeding on germinating seeds, buds, and developing fruit. Smith, B. J.; Lockley, T. C. *J. Entomol. Sci.* 1993, 28, 236–239. To make matters worse, fire ants do not harm mealy bugs, which damage many types of crops. These problems are unfortunately worse in drought weather when the ants supplement their water intake with plant matter. Remarkably, fire ants have been known to destroy farm equipment because of their large numbers. For example, by crowding between parts, fire ants have removed insulation from wires and blocked the action of mechanical devices. MacKay, W. P.; Vinson, S. B. *Applied Myrmecology: A World Perspective*. Eds. Robert Vander Meer, Klaus Jaffe, Aragua Cedeno. 1990, Westview Press, Boulder, 614–619. Moreover, fire ants have been blamed for infrastructure damage; when they have built their nests under roads, the roads have been known to collapse. One of the biggest industrial problem is with electric power companies—approaching $1 million or more a year in Georgia alone.

Attempts of Fire Ant Suppression by Chemical Methods

Since the early 1950's, insecticides have been the primary method of choice to control fire ants. There are three broad classes of insecticides for fire ants: (1) the contact insecticides, which enter the ant through the skin; (2) the stomach insecticides, which are ingested; and (3) the fumigants, which are inhaled.

The contact insecticides typically destroy the imported fire ants within one week by way of their residues. Although they work quickly, their application is too difficult for use in large areas with numerous mounds. Consequently, they are only suited for small areas such as backyards. Banks, W. A. *Applied Myrmecology: A World Perspective*. Eds. Robert Vander Meer, Klaus Jaffe, Aragua Cedeno. 1990, Westview Press: Boulder, Colo., 596–603. As a whole, these insecticides are 80% effective, but if they do not kill all the ants after one application, the survivors will build new mounds, and reapplication will be necessary. There are two main groups of contact insecticides: (1) the chlorinated hydrocarbons and (2) the organophosphates.

The first methods of chemical control of *S. invicta* employed the use of chlorinated hydrocarbons, such as heptachlor and dieldrin. Lofgren, C. S. *Fire ants and Leaf-cutting ants: Biology and Management*. Eds. Clifford Logren and Rober Vander Meer. 1986, Westview Press: Boulder, Colo. 36–47. These synthetic pesticides were advantageous because they were inexpensive and very effective against a variety of insects. Furthermore, they were not easily broken down by enzymes, microorganisms, heat, or light, so they would work long after application. However, like DDT, a related chlorinated hydrocarbon, these pesticides were poisonous to a variety of diverse wildlife, and they accumulated in fat tissues so that they were distributed throughout the food chain. Consequently, these insecticides' use was subsequently halted.

The second class of contact pesticides used in the control of fire ants are the organophosphates, which are inhibitors of the enzyme acetylcholine esterase. The use of these compounds results in the buildup of acetylcholine, which leads to tremors, muscular spasms, convulsions, and eventually death. They work rapidly, and are inexpensive to apply in low-density areas. Vinson, S. B.; Sorensen, A. A. *Imported Fire Ants: Life History and Impact*. 1986, Texas Department of Agriculture, Austin, 7–20. The organophosphates are all derivatives of phosphoric acid. The most effective aliphatic analogues are tetraethyl pyrophosphate (TEPP) and malathion. Pedigo, L. P. *Entomology and Pest Management*. 1989, MacMillan, N.Y., 364–376.

Organophosphates can be applied as aerosols, granules, dusts, or drenches. They decompose into nontoxic substances in sunlight and are therefore safer than the chlorinated hydrocarbons. But they still are toxic enough that application to each mound is necessary, rather than scattering the insecticide everywhere. This labor-intensive type of application is obviously not appropriate for large or densely infested regions. Another drawback of organophosphates is they are not species-specific, and consequently all ants in a treated area may be destroyed. This is a disadvantage because after the compound breaks down, the area may become reinfested if adjacent areas are not treated. If the competitors are exterminated, it will allow the fire ant to re-establish itself at greater levels than before the treatment. Vinson, S. B.; Sorensen, A. A. *Imported Fire Ants: Life History and Impact*. 1986, Texas Department of Agriculture, Austin, 7–20.

Citrus oils are the only naturally occurring contact insecticides used in fire ant control. Ellis, B. W.; Bradley, F. M. *The Organic Gardener's Handbook of Natural Insect and Disease Control: A Complete Problem-Solving guide to Keeping Your Garden & Yard Healthy Without Chemicals*. 1992, Rodale Press: Emmaus, Pa., 467–470. The active components have been found to be (S)-limonene and linalool. These compounds are very effective on fire ants that contact them immediately, but they quickly decompose. Olkowski, W.; Daar, S, Okowski, H. *Common-Sense Pest Control: Least Toxic Solutions for Your Home, Garden, Pets, and Community*. 1991, Taunton Press: Newton, Conn., 124. This obviously limits their long term efficacy.

One of the fastest developing group of contact insecticides are pyrethroids. Pedigo, L. P. *Entomology and Pest Management*, 1989, MacMillan, N.Y., 364–376. They are very stable to light and heat. Most importantly, pyrethroids are non-toxic to the environment and they are very effective in exterminating fire ants. Some of the newest members of this class that have shown very promising activity are flucythrinate and fluvalinate.

In contrast to the contact poisons, stomach insecticides are fatal only after they are ingested. Unlike the chlorinated hydrocarbons, stomach insecticides are combined with bait before being distributed. The main disadvantage of this method is that it takes a relatively long time before results can be seen. The most infamous stomach insecticide used in the eradication of fire ants was the chlorinated hydrocarbon Mirex.

Mirex was inexpensive and more than 95% effective. Also, unlike the other chlorinated hydrocarbons such as heptachlor and dieldren, Mirex left no chemical residues, so it was much safer. Lofgren, C. S. *Fire ants and Leaf-cutting ants: Biology and Management*. Eds. Clifford Logren and Rober Vander Meer. 1986, Westview Press: Boulder, Colo. 36–47. Like many other treatments, it killed all ground-nesting ants, so any reinfestation from an adjacent area were dominated by *S. invicta*. Nevertheless, the primary drawback of this method was that Mirex, like other chlorinated hydrocarbons, accumulated as it moved through the food chain. Hence, by 1977 it was no longer in use.

Another commonly used stomach insecticide is boric acid, $B(OH)_3$. Usually, it is delivered in some sort of bait such as sugar, jelly, or pet food. Ellis, B. W.; Bradley, F. M. *The Organic Gardener's Handbook of Natural Insect and Disease Control: A Complete Problem-Solving guide to Keeping Your Garden & Yard Healthy Without Chemicals*. 1992, Rodale Press: Emmaus, Pa., 467–470. It does not specifically target fire ants. Even more discouraging is that fire ants are not as susceptible to the poison as are other ant species. Olkowski, W.; Daar, S, Okowski, H. *Common-Sense Pest Control: Least Toxic Solutions for Your Home, Garden, Pets, and Community*. 1991, Taunton Press: Newton, Conn., 124. As a result, boric acid is only appropriate for very small scale problems.

Modern toxic baits are very effective forms of stomach insecticides for *S. invicta*. The two toxic baits available today are Amdro and Affirm. As a whole, modern toxic baits are less toxic than most contact poisons registered for fire ants. Because it is easier to get to the queen, reinfestation by members of the same colonies is less likely than with the use of toxic poisons. Since there are tunnels that may extend as far as twenty-five feet in length from the mound to be used by fire ants when looking for food, the bait needs to be dispersed over the entire area. One disadvantage of toxic baits is that the ants may take too long to find the bait before light and heat decompose it. Vinson, S. B.; Sorensen, A. A. *Imported Fire Ants: Life History and Impact*. 1986, Texas Department of Agriculture, Austin, 7–20. Like most of the other chemical control methods, toxic baits are not specific to fire ants.

Because of the obvious ineffectiveness of chemical control of fire ants by the aforementioned procedures, attention has been turned to biological controls such as sterile insect release, insect growth regulators, and natural enemies of RIFA.

The sterile insect release method has been used successfully to control other pests. Sterile males are released into the population, and this reduces birth rates. Whitten, M. J.; Foster, G. G. *Annual Review of Entomology*. 1975, 20, 461–176. Unfortunately, this method works best on insects that are not as abundant as fire ants, since so many more males would have to be released into the population. Moreover, fire ants breed up to nine months annually, so it would be difficult to breed the required number of sterile male ants. Lofgren, C. S. *Fire ants and Leaf-cutting ants: Biology and Management*. Eds. Clifford Logren and Rober Vander Meer. 1986, Westview Press: Boulder, Colo. 36–47.

Insect growth regulators (IGRs) overload the ants' hormonal system, which reduces or halts egg production. Glancey, B. M.; Reimer, N.; Banks, W. A. *Applied Myrmecology: A World Perspective*. Eds. Robert Vander Meer, Klaus Jaffe, Aragua Cedeno. 1990, Westview Press: Boulder, Colo., 604–613. Furthermore, IGRs affect care of offspring and other social interactions, and prevent worker ants from reaching adulthood. Usually treatment with IGRs are over 85% effective, even in multi-queen colonies. Banks, W. A. *Applied Myrmecology: A World Perspective*. Eds. Robert Vander Meer, Klaus Jaffe, Aragua Cedeno. 1990, Westview Press: Boulder, Colo., 596–603. In addition, they do not affect other animals or even other species of ants. Stall, G. B. *Annual Review of Entomology*. 1975, 20, 417–460. The most commonly used insect growth regulator is fenoxycarb, the active ingredient in commercially available Logic.

Two shortcomings are that natural juvenile hormones are unstable in sunlight and insect growth regulators are very expensive. Stall, G. B. *Annual Review of Entomology*. 1975, 20, 417–460. Probably the biggest disadvantage of the IGRs is the relative non-toxicity to adult fire ants, so the colonies die in four to six months, or the length of the worker adult life span. Vinson, S. B.; Sorensen, A. A. *Imported Fire Ants: Life History and Impact*. 1986, Texas Department of Agriculture, Austin, 7–20.

When RIFA were introduced into North America, very few of their natural enemies were introduced. Jouvenaz, D. P. *Florida Entomology*. 1983, 66, 275–279. Accordingly, one strategy of biological control of fire ants is the introduction of their natural enemies. Jemal, A.; Jones, M. H. *Preventive Veterinary Medicine*, 1993, 17, 19–32. The ideal candidates for this tactic are those pests that have themselves migrated from other areas. Current research has focused on ants, nematodes, and fuigi as potential candidates for natural enemies of the fire ant. Jouvenaz, D. P. *Applied Myrmecology: A World Perspective*. Eds. Robert Vander Meer, Klaus Jaffe, Aragua Cedeno. 1990, Westview Press: Boulder, Colo., 620–627. Predators such as dragonflies are known to strike fire ant queens during and just after their mating flights. Vinson, S. B.; Sorensen, A. A. *Imported Fire Ants: Life History and Impact*. 1986, Texas Department of Agriculture, Austin, 7–20. Unfortunately, these methods have only been applicable to stable environments such as orchards and forests, and fire ants prefer disturbed areas that can be easily exploited. In spite of this fact, much research is being conducted to find enemies of *S. invicta* to aid in its control. Usually natural enemies only affect a small group of insects, sometimes even a single species, so consequently this is an extremely safe method for the environment. The major drawback from using this method is that the natural enemy might quickly spread on its own.

Pathogens of *S. invicta* have been tested and found not to be very effective with the exception of a fungus isolated from the fire ants in Brazil. These fungi nutritionally burden the fire ants, and could be mass-produced if necessary. Recent investigations may involve genetic engineering of fungi to produce substances that damage the ants even more. Jouvenaz, D. P.*Applied Myrmecology: A World Perspective*. Eds. Robert Vander Meer, Klaus Jaffe, Aragua Cedeno. 1990, Westview Press: Boulder, Colo., 620–627.

Another means of biological control is the introduction of parasites. Insect parasites lay their eggs in the eggs or adults of the host so their larvae can feed on the host tissue. They are parasitic in their immature stages only and always kill their hosts. Advantages of using parasites as a biological control are that they have a high survival rate and they usually affect only a narrow range of insect species. Drawbacks include that changing weather varies their effectiveness, only the female searches, and the best searchers lay few eggs. Pedigo, L. P. *Entomology and Pest Management*, 1989, MacMillan, N.Y., 364–376. Furthermore, synchronization is important, as certain environmental conditions might cause the parasite to fail to reduce host numbers significantly. Research is being conducted now on phorid flies as potential parasites to the RIFA. Feener, D. H. *Science*. 1981, 214, 815–817. There are also social parasites, which invade the ant colony as a whole, rather than individual ants. An example is the socially-parasitic ant queen, which is known to move into exisiting fire ant colonies, and get cared for by its own workers, in preference to their own queens. Also, this species invades only fire ant mounds, so it is species-specific. Because socially parasitic queens do not produce their own workers, the nest will deteriorate very slowly. Jouvenaz, D. P. *Applied Myrmecology: A World Perspective*. Eds. Robert Vander Meer, Klaus Jaffe, Aragua Cedeno. 1990, Westview Press: Boulder, Colo., 620–627. Generally, the fire ant colony collapses within two years, so this method is not practical for rapid extermination. Another example of a social parasite to fire ants are the myrmecophile beetles. These beetles can integrate into colonies of different fire ant species and eat ant larvae, undigested ant food, or get the ants to feed them. Through a system of mimicry, the bettles develop hydrocarbon shells that match those of the specific type of ant they are invading. Jouvenaz, D. P. *Applied Myrmecology: A World Perspective*. Eds. Robert Vander Meer, Klaus Jaffe, Aragua Cedeno. 1990, Westview Press: Boulder, Colo., 620–627. Moreover, they can mimic their host's behavior and communication system.

All of these prior art methods suffer from one or more inadequacy, the most common being that the approach is not specific to fire ants. Thus, there is a current need for a method of eradicating or limiting the spread of fire ant colonies using novel chemical approaches, which are specific, fast, effective and inexpensive. One of these methods involves the use of solenopsin derivatives as inhibitors of venom production in fire ants.

The use of solenopsins for the elimination of ticks, fleas or other parasitic infections in dogs and cats has been disclosed by Rehmert et al. in U.S. Pat. Nos. 4,910,209, 5,075,320, and 5,098,914. In this approach, the solenopsins may be administered from the whole body extract of the insect or from an oral dosage form containing more highly purified material. The administration of these drugs over a period of one to eleven days with regular booster dosages disseminates the alkaloid composition through the blood and tissue fluids of the treated animals and eliminates fluid-feeding parasites.

In the whole body version, the insects are ground to a fine texture, inserted into soluble capsules as whole body extract along with an edible carrier material such as fish oil, and are kept frozen until administration. The venom is kept refrigerated in order to maintain its effectiveness. Additionally, each insect is considered to contain approximately one venom unit or 40 nanoliters of the solenopsins, Solenopsin A and Solenopsin B.

Typically, 100–400 units of such extracts are given consecutively to dogs weighing four to 120 pounds over 11 days. However, day two is skipped to allow the animal to react to the dosage. Complete elimination of tick and flea infestation was achieved. Similarly, 100– 200 units were administered in cats as well and resulted in same results. Booster doses are also given monthly in order to prevent re-infestation of such parasites.

Synthetically produced Solenopsin A is effective as well and results in complete elimination of blood and tissue- and fluid-feeding parasites. Unlike the whole body extract, it does not require refrigeration. However, higher number of units of the synthetic version are required for effective treatment. For example, 1500 units of synthetically produced Solenopsin A are equivalent to 250 units of the whole body extracts. As much as 6000 units of Solenopsin A has been used over a shorter time period and did not cause any ill effects.

Oral dosage capsules in the range of 1500 units are typically prepared by mixing 50–60 microliters of Solenopsin A with 0.1 ml of isopropylalcohol, 20 mg of fumed silica and 150 mg of microcrystalline cellulose as a carrier material. They are then packaged into soluble capsules.

The solenopsins have demonstrated low toxicity and also have shown to be more effective than the organophosphates whose efficacy has decreased due to the development of resistance in parasites. Furthermore, they are also excellent alternatives to the organophosphates which are toxic to cats.

OBJECTS OF THE INVENTION

It is therefore an object of the present invention to provide solenopsin derivatives for use in inhibiting venom production in *Solenopsis invicta*.

It is another object of the present invention to provide compositions comprising effective amounts of at least one solenopsin derivative according to the present invention which may be used to inhibit the production of venon in *Solenopsis invicta*, resulting in a reduction in the population of *Solenopsis invicta* as a consequence of the fire ant having reduced venom and fewer defenses against natural predators.

It is an additional object of the present invention to provide a method of inhibiting the production of venom in *Solenopsis invicta* and limiting the growth of or eradicating a population of fire ants using compositions according to the present invention.

These, and or other objects of the present invention may be readily gleaned from a description of the present invention or the numerous embodiments which follow.

BRIEF DESCRIPTION OF THE INVENTION

The present invention relates to solenopsin alkaloid derivatives which are trans-2,6-disubstituted piperidines according to the structure:

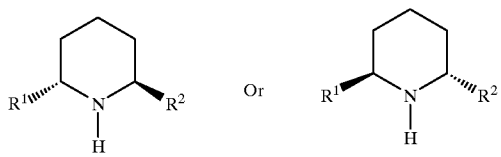

wherein $R^1$ and $R^2$ are selected from a $C_1$ to $C_{20}$, preferably a $C_2$ to $C_9$ saturated or unsaturated linear, cyclic or branch-chained substituted or unsubstituted alkyl group or a substituted or unsubstituted aromatic group. The above-mentioned alkyl group may be substituted with a substituted or unsubstituted aromatic group (an example of such a group would be a benzyl group). In addition, each of $R^1$ and $R^2$ may be an ester group, preferably, a $C_1$ to $C_6$ alkyl ester group. In preferred embodiments, where $R^1$ or $R^2$ contains an unsaturated group, such as an alkenyl group, the double bond preferably is found in the alkyl chain between the carbon atom bonded to the piperidine ring and the adjacent carbon atom ($\alpha$ and $\beta$ carbons). Where either $R^1$ or $R^2$ is a saturated or unsaturated hydrocarbon group (for example, an alkyl or alkenyl group) or an ester group, the other of $R^1$ or $R^2$ is preferably a methyl group. The present compounds may be used in their neutral form, or more preferably, as their more water soluble salt forms.

In the present compounds, $R^1$ and $R^2$ are preferably straight or branch-chained alkyl or alkenyl groups, cyclic alkyl groups such as cyclopentyl or cyclohexyl groups, alkylphenyl or alkenyl phenyl groups or alkyl ester alkanoate or alkyl ester alkenoate groups.

Figure 1:
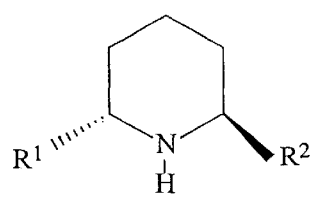
FIG. 1 is a diagrammatic representation of preferred compounds according to the present invention. The figure depicts the basic piperidine structure with two substituents $R^1$ and $R^2$ along with a number of alkyl, alkenyl, alkylbenzene and alkyl ester groups which are preferred substituents for compounds according to the present invention.
Figure 1:
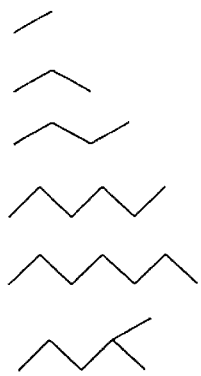
Figure 1:
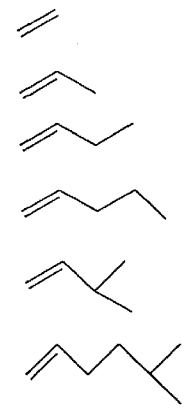
Figure 1:
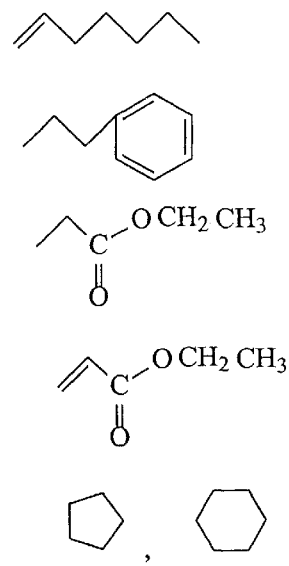

$R^1$ and $R^2$ are more preferably selected from the group consisting of methyl, ethyl, propyl, butyl, pentyl, hexyl, heptyl, 4-methylpentyl, 5-methylhexyl, cyclopentyl, cyclohexyl, vinyl, propenyl, butenyl, pentenyl, hexenyl, heptenyl, 3-methylbutenyl, 5-methylhexenyl, benzyl, ethylbenzene, propylbenzene, ethyl propanoate and ethyl propenoate. A number of these preferred groups are depicted diagrammatically in attached FIG. 1.

The present invention also relates to novel compositions comprising an effective amount of one or more solenopsin analogue according to the present invention as described above in combination with a fire ant bait, which may be spread in various locations in proximity to a fire ant colony. In this aspect of the present invention, the solenopsin analogue in combination with the fire ant bait is spread at or near the fire ant colony and the fire ants, attracted to the bait, will then carry the solenopsin analogues to other fire ants within the fire ant colony. Upon ingesting the bait containing the solenopsin analogues, the fire ants will experience a reduction in the production of venom, which will make them much more likely to succumb to predation by any number of natural predators.

The present invention also relates to methods of controlling the growth of or spread of fire ant colonies comprising exposing a fire ant colony to an effective amount of one or more solenopsin compounds according to the present invention alone, or preferably in combination with a fire ant bait.

A method of repelling insects is an additional aspect of the present invention. In this aspect of the present invention, one or more compounds according to the present invention which mimics the sensory effects of solenopsin A or B in repelling insects, may be used as an insect repellent. In this aspect of the present invention, an effective amount of one or more analogues of solenopsin are placed in a carrier or vehicle and are then delivered to or spread on areas from which insects susceptible to solenopsin A or B are to be repelled, resulting in a marked decrease in insects in the treated area. It is an unexpected result that certain compounds according to the present invention may be used as compositions for repelling a number of insects susceptible to the effects of solenopsin.

Compounds and compositions according to the present invention may be used to inhibit the production of venom of Solenopsis invicta, in certain instances, mimic the venom of Solenopsis invicta, provide insight into the structure activity relationship of piperidine compounds and other compounds which may exhibit biological activity in Solenopsis invicta. By inhibiting production of venom in Solenopsis invicta, the present compounds indirectly serve to control the population of, inhibit the spread of or even eradicate colonies of Solenopsis invicta. This is an unexpected approach to controlling populations of the fire ant. Compounds according to the present invention may also be used to repel insects susceptible to the effects of solenopsin from an area treated with an effective amount of a solenopsin analogue according to the present invention.

DETAILED DESCRIPTION OF THE INVENTION

As used herein, the following definitions shall be used to describe the present invention.

The term "fire ant" and "Solenopsis invicta" are used interchangably to describe the common red fire ant, originating in South America, but now commonly found in 11 southeastern states of the United States, parts of the southwestern United States, California, and Puerto Rico. The term fire ant may also be used to describe black fire ants and other hybrid fire ants or other ants which produce solenopsin venom.

The term "compound" or "active compound" is used to describe any one or more of the active 2,6-disubstituted piperidine compounds which exhibit activity against "Solenopsis invicta" in the present invention.

The term "composition" is used to describe a composition which contains a compound according to the present invention, a bait and optionally, a carrier.

The term "water soluble salt form" or "salt form" is used to describe forms of compounds according to the present invention which are in their water soluble salt form. Salt forms of compounds according to the present invention include any salt which retains the desired biological effects. Nonlimiting examples of such salts are acid addition salts formed with inorganic acids such as hydrochloric acid, hydrobromic acid, sulfuiric acid, phosphoric acid, nitric acid and the like, salts formed with organic acids such as acetic acid, oxalic acid, tartaric acid, succinic acid, malic acid, ascorbic acid, benzoic acid, tannic acid, pamoic acid, alginic acid, glutamic acid, naphthalenesulfonic acids, naphthalenedisulfonic acids and glacturonic acid, among numerous others. Salts may be formed by neutralizing the nitrogen on the piperidine ring with the resulting salts exhibiting substantially greater solubility or derliverability of the instant compounds. These may also affect the bioavailability and rate of metabolism or stability of the compounds according to the present invention.

The term "inhibitory effective concentration" or "inhibitory effective amount" is used throughout the specification to describe concentrations or amounts of compounds according to the present invention which substantially or significantly inhibit the biosynthesis of venom and in particular, Solenopsin A and B, from Solenopsis invicta. The inhibition of the biosynthesis of Solenopsin A and B of the fire ant, results in fire ants so exposed to compounds according to the present invention, becoming more susceptible to natural predators, with the result being a diminution in and/or eradication of a population of fire ants. Inhibitory effective concentrations or amounts of the present compounds are also useful for preventing the spread of colonies of the fire ant.

The term "repelling effective amount" is used throughout the specification to describe concentrations or amounts of compounds according to the present invention which are used to repel insects and other animals which are susceptible to the venom of Solenopsis invicta.

The term "preventing effective amount" is used throughout the specification to describe concentrations or amounts of compounds according to the present invention which are used to prevent the spread of colonies of fire ant. In many instances, a preventing effective amount and an inhibitory effective amount of one or more of the compounds according to the present invention fall within the same concentration ranges.

The term "effective amount" shall mean an amount or concentration of a compound according to the present invention which is effective within the context of its use as an inhibitor of venom production, fire ant colony formation, as a repellent compound or in other uses.

The term "pure" is used to describe a compound according to the present invention which has been synthesized and/or isolated and is not found in its natural state. Pure compounds according to the present invention are those which preferably comprise at least 95% by weight of the desired compound, more preferably at least about 97–98% by weight of the desired compound and even more preferably about 99+% by weight of the desired compound. Pure compounds according to the present invention, are distinguished from compounds which may be found in their natural state, for example, as the metabolic products of biosynthesis by a living organism. Pure compounds include those natural products which have been isolated from an organism and are in a form which is used to deliver active compound for the purposes which are otherwise described in this patent application.

The term "enantionmerically enriched" is used throughout the specification to describe a compound which includes at least about 95%, preferably at least about 96%, more preferably at least about 97%, even more preferably, at least about 98%, and even more preferably at least about 99% or more of a single enantiomer of the described compound. Where the enantiomeric enrichment of a compound is unstated, it is presumed (unless the synthetic chemistry dictates otherwise) that the compound is a racemic mixture.

The term "hydrocarbon" is used to describe a group or radical which is bonded to piperidine at the 2 and 6 positions which contain carbon and hydrogen atams. A hydrocarbon according to the present invention ranges from a $C_1$ to $C_{20}$ hydogen and preferably is directed to a $C_2$ to $C_9$ hydrogen, more Hydrocarbon groups according to the present invention may be linear, branch-chained, cylic, saturated or unsatured, substituted or unsubstituted. Subsumed under the term hydrocarbon are the terms "alkyl", "alkenyl" and "aromatic".

The term "alkyl" is used to describe is used to describe a $C_1$ to $C_{20}$ hydrocarbon group which is saturated, linear, branch-chained or cyclic. Exemplary alkyl groups for use in the present invention include methyl, ethyl, propyl, butyl, pentyl, hexyl, heptyl, cyclopentyl, cyclohexyl, 5-methylhexyl, 4-methylpentyl, among others. Preferred alkyl groups are $C_1$–$C_9$ (in the case of groups substituted on the 2 and 6 postions of the piperidine of compounds according to the present invention) alkyl groups, which may be substituted or unsubstituted, linear, branch-chained or cyclic.

The term "alkenyl" is used to describe a hydrocarbon group which contains a single unsaturated group or carbon-carbon double bond (C=C). In preferred aspects of the present invention, the carbon-carbon double bond of unsaturated (including alkenyl) substituents occurs on the carbon which is bonded to the piperidine ring and the adjacent carbon in the substituent side chain.

The term "unsubstituted" shall mean that a hydrogen group or hydrocarbon groups are bonded to the carbon atoms in the side-chain to the exclusion of substituted groups, for example, halogen groups.

The term "substituted" shall mean in all instances, halogen groups, in particular, fluorine, chlorine, bromine and iodine groups. In the case of aromatic groups, substituted groups may also include, for example, one or more $C_1$ to $C_3$ alkyl groups, as well as halogen groups, which are attached to aromatic groups, for example a phenyl group. In the case of alkyl or alkenyl groups, substituted groups may also include one or more substituted or unsubstituted alkyl group.

The term "aromatic" is used to refer to groups which contain an unsaturated six membered ring, such as a phenyl group or benzene ring. Aromatic groups for use in the present invention include substituted or unsubstituted phenyl groups or groups which contain benzene rings. Substituted aromatic groups are those which contain at least one alkyl or alkenyl group or a halogen group (I, Br, Cl or F) and up to five of such groups.

The term "ester" is used to describe a group which contains an ester group or

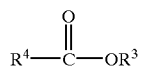

group which may be used an $R^1$ or $R^2$ substituent on the piperidine ring of the present where $R^4$ is a —$(CH_2)_n$— group or a group containing at least one double bond such as a —CH=CH—$(CH_2)_{n-2}$— where n is from 1 to 20, preferably from 1 to 6 and $R^3$ is a $C_1$ to $C_6$ alkyl group, preferably a $C_1$ to $C_3$ alkyl group.

The term "bait" is used to describe a carrier which is an attractant to fire ants. Preferred baits include food products or other materials which attract or draw fire ants to it and which the fire ant ingests or takes back to its colony so that other fire ants may ingest the material. As used herein, the term bait shall be directed to any material which is sought after by a fire ant and includes numerous types of insect bait. The term bait includes, for example, any material or substance which is formulated or may be formulated for the biology, feeding behavior and food preferences of fire ants and includes materials which contain, for example, any one or more of sucrose, fructose, proteins, peptides, amino acids, and different salts and minerals and other materials which the fire ant obtains from the environment. Suitable baits can include for example, sugar, jelly, peanut oil, soybean oil, corn oil, other vegetable oils, peanut butter, honey, and related food items, including grains, cereals, soy protein etc.

Compositions for use as agents for suppressing the biosynthesis of the venom of fire ants and for reducing and/or eradicating the population and preventing the spread of colonies of fire ants according to the present invention comprise an effective amount of one or more compounds according to the present invention in combination with a bait and optionally, a carrier (preferably, an inert, non-repellent carrier) for delivering the composition to a desired site. The term non-repellent carrier is used to describe carriers which aid the delivery of the present compounds and bait to a site of delivery without repelling the fire ants from ingesting or otherwise utilizing the bait and compound. Non-repellent carriers include water, other non-repelling solvents such as water and minor quantities of ethanol and other carriers which do not specfically attract fire ants, but may include items which provide a minor source of nutrition for the fire ant. Carriers for use in the present invention include such materials as corn cob grits, defatted corn cob grits, degermed corn cob grits, extruded corn pellets, among others. Exemplary baits are described in U.S. Pat. Nos. 5,900,243; 5,897,859; 5,850,707; 5,690,951; 5,837,273; 5,571,522; 5,484,599; 5,104,658; 4,985,413; and 4,983,390, all of which are incorporated by reference hereof.

Compositions according to the present invention include about 0.001% to about 99% or more by weight of the composition including the bait, with a preferred composition including about 0.1% to about 40% by weight of the present compound and the remainder comprising a fire ant bait and optionally, a non-repellent carrier. Even more preferred compositions according to the present invention comprise about 0.5% to about 20% by weight of a compound according to the present invention and the remainder comprising a bait and optionally, a non-repellent carrier. In certain preferred compositions according to the present invention, the amount of active compound comprises about 0.5% to about 10% by weight, the amount of bait comprises about 10% to about 30% by weight, and the amount of inert, non-repellent carrier comprises about 60% to about 89.5% by weight of the composition.

| | |
|---|---|
| $Ac_2O$ | acetic anhydride |
| $Boc_2O$ | di-tert-butyl dicarbonate |
| Cbz-Cl | benzyl chloroformate |
| DMF | N, N'-dimethylformamide |
| EtOAc | ethyl acetate |
| LAH | lithium aluminum hydride |
| LDA | lithium diisopropylamide |
| MsCl | methanesulfonyl chloride |
| NMP | N-methyl-2-pyrrolidone |
| TBS-Cl | tert-butyl-dimethylchlorosilane |
| t-BuOK | potassium tert-butoxide |
| TEA | triethylamine |
| TFA | trifluoroacetic acid |
| THF | tetrahydrofuran |
| THP | tetrahydropyran |
| TMEDA | N,N,N',N'-tetramethylethylenediamine |
| TsCl | para-toluenesulfonyl chloride |
| TsOH | para-toluenesulfonic acid |

In the present methods, in order to reduce or eradicate a population of fire ants and to inhibit or prevent the spread of fire ant colonies, the present compositions are delivered to the fire ant by spreading the composition at or near the fire ant colonies. The amount of composition used is an effective amount for producing the intended result, whether to inhibit or eradicate the population of fire ants or to inhibit or prevent the spread of fire ant colonies.

In a method of inhibiting the production of venom by the fire ant, an effective amount of one or more compound according to the present invention may be applied liberally in any area at or near the fire ant colony to be eradicated. Depending upon the carrier, which may be solid or liquid, an effective amount of the present compound in an appropriate carrier (which itself may be the fire ant bait) is delivered to a site at or near enough to the fire ant colony so that the a number of fire ants will be attracted to the bait and bring it back to the ant colony for consumption by other ants in the colony. Although the amount of composition used as well as the active compound, bait and carrier included within the composition will vary broadly depending upon the size of the ant colony, the number of colonies involved and the terrain of the area nearest ant colonies, preferably, an effective amount of composition will range from about 100 grams to about 5 kilograms or more per acre, with each of the active compound, bait and optional carrier varying depending upon the requirements of a particular treatment.

Compositions according to the present invention may be readily prepared by dissolving compounds according to the present invention in water or an appropriate solvent (such as a water/ethanol mixture) as carrier and then mixing the compounds in solvent with bait to a desired level. Alternatively, active compounds may be admixed with solid bait and optionally, carrier to produce compositions useful in the present invention. Other methods of making compositions according to the present invention will be readily apparent to one of ordinary skill in the art.

Chemical Synthesis of Active Compounds

The present compounds are synthesized using general methods which are well known in the art. An efficient flexible chemistry may be used to synthesize Solenopsin A and analogues from Solenopsin A. The method reported by D. Comins may be used and adapted for a number of analogues according to the present invention. Comins, D. L.; Weglarz, M. A. *J. Org. Chem.* 1991, 56, 2506.

Figure 2:
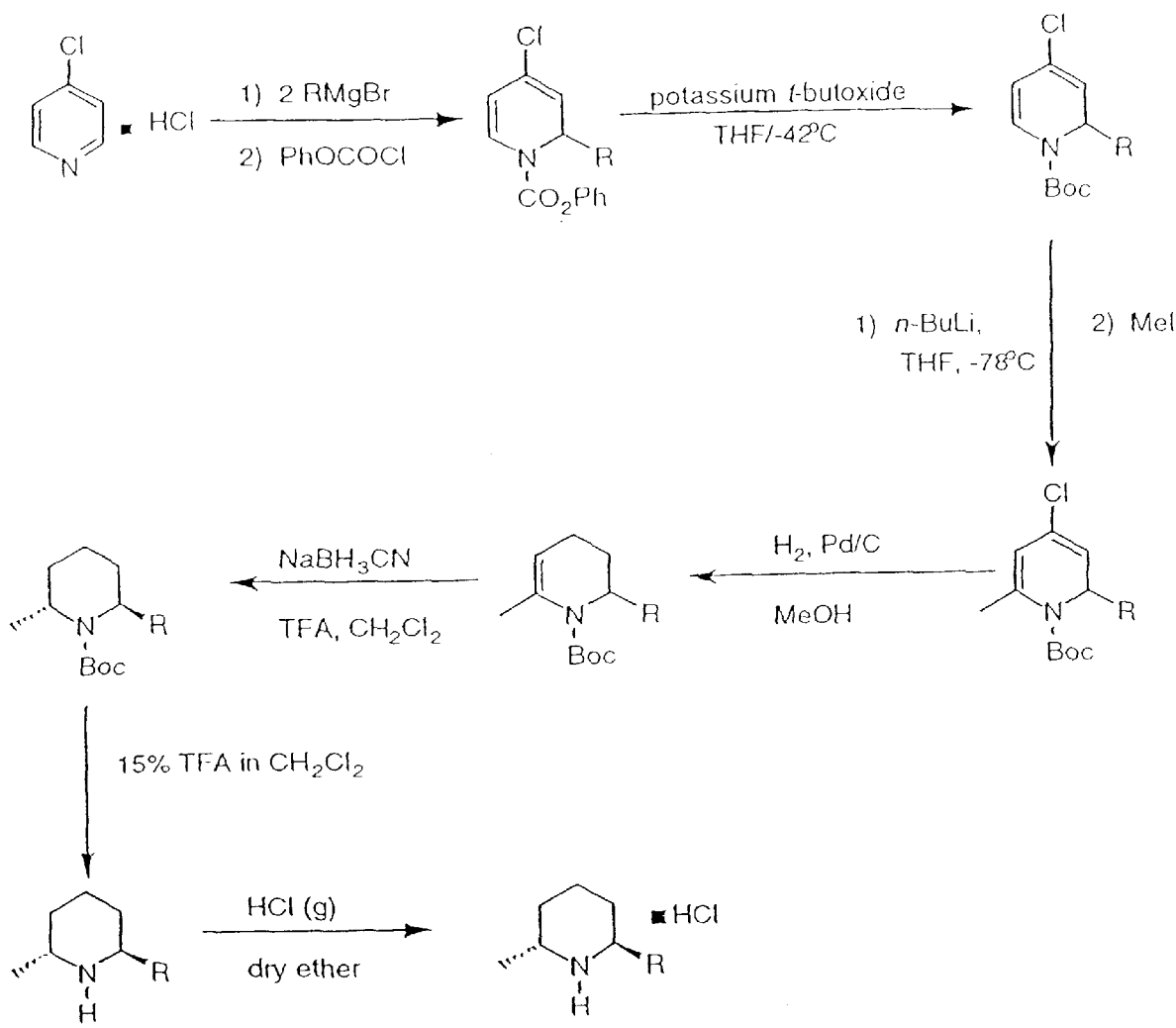
FIG. 2 is a diagramatic representation of the chemical synthesis of certain analogues according to the present invention (where $R^1$ is $CH_3$ and R is $S_1$, $S_2$ or $S_3$ as indicated) according to Scheme I.

The Comins methodology for synthesis of solenopsin A and its analogues is set forth diagrammatically in FIG. 2, Scheme I. In this method, 4-chloropyridine undergoes introduction of an R group at the 2-position of the pyridine ring using alkylmagnesium bromide in THF at −78° C. followed by treatment with phenylchloroformate to provide the respective dihydropyridine derivative. The dihydropyridine derivative is then converted into the corresponding N-Boc (Boc is a tertiary butyl carbonate group) derivative using potassium t-butoxide in tetrahydrofuran and −42° C. A methyl (or other alkyl group) is introduced into the 6 positoin of the dihydropyridine ring as indicated by utilizing a first step of n-BuLi in THF at −78° C. followed by introduction of the methyl (alkyl) group at the 6 position of the dihydropyridine compound utilizing methyliodide to form the dialkyl substituted chlorine substituted dihydropyridine derivative as indicated. The dialkyl substituted chorine substituted dihydropyridine derivative is then subjected to a hydrogenation procedure (hydrogen, palladium/carbon catalyst in methanol) to remove the chlorine group at the 4 position as indicated, which derivative is further hydrogenated using $NABH_3$/TFA in methylene chloride to provide the dialkyl substituted N-boc piperidine derivative. The boc group may be readily removed using 15% trifluoracetic acid in methylene chloride to afford the dialkyl substituted piperidine derivative. Salt formation may readily occur as indicated using the appropriate acid to acidify the basic nitrogen.

In an alternative chemical synthetic method, a more efficient route to the dialkyl substituted piperidine analogues according to the present invention is used. This route also allows the facile introduction of a double bond in the side chain of the 2 position of the piperidine ring. The method follows the chemical methods which are reported by Beak, et al. See Beak, P.; Lee, W. K. *J. Org. Chem.* 1993, 58, 1109 and *Tetrahedron Lett.* 1989, 30, 1197. This method demonstrated a regioselective and diastereoselective method for a lithiation-substitution at a methylene group.

Figure 3:
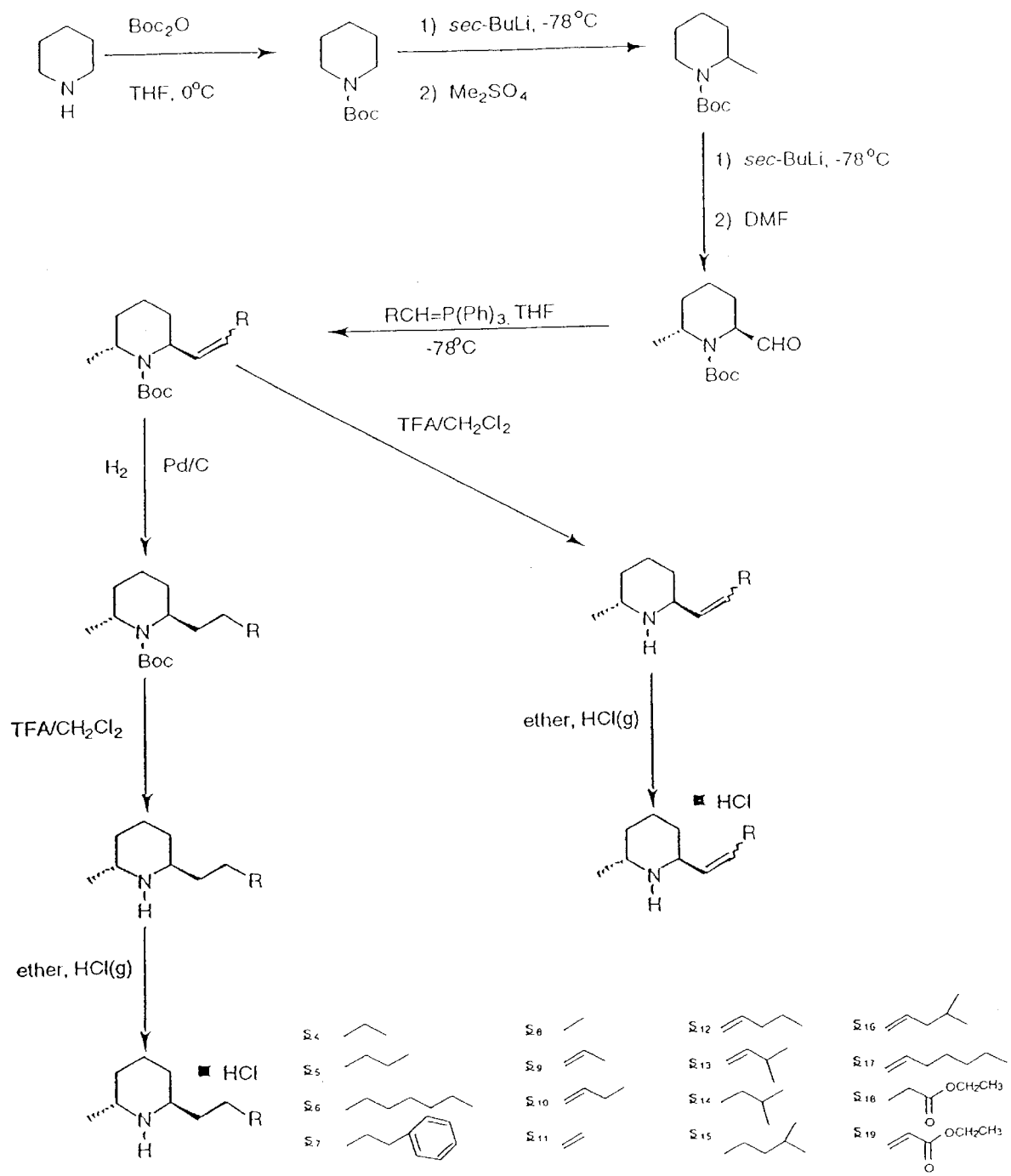
FIG. 3 is a diagramatic representation of the chemical synthesis of certain analogues according to the present invention (where $R^1$ is $CH_3$ and R is $S_4$–$S_{19}$ as indicated) according to Scheme II.
Figure 4:
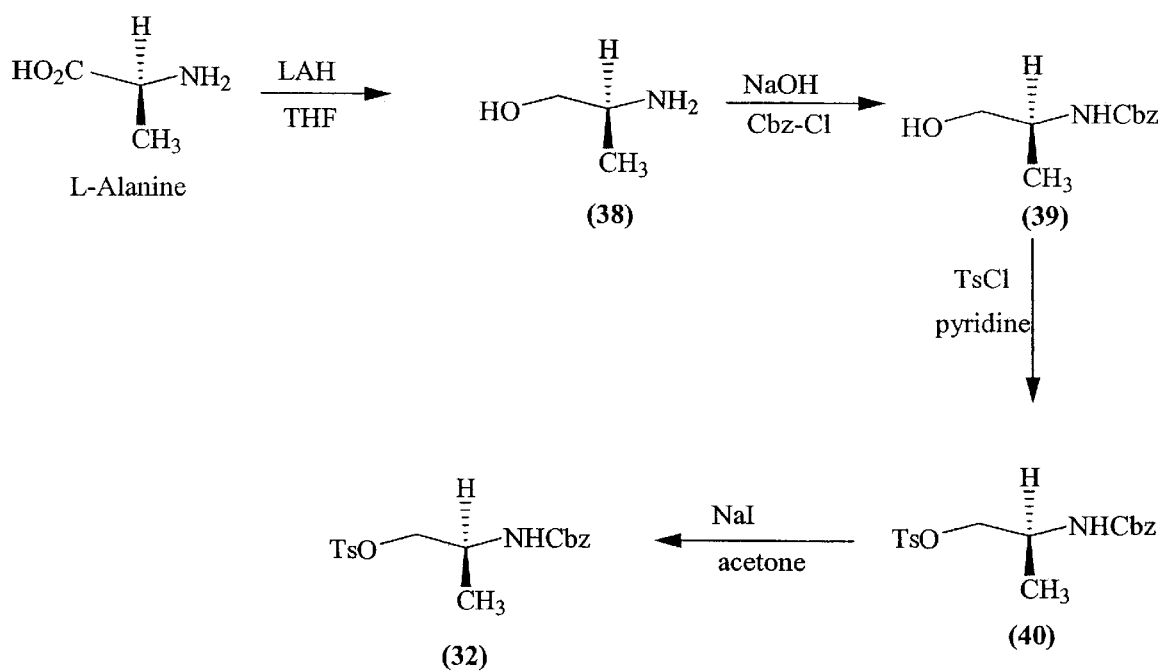
FIG. 4 is a diagrammatic representation of an alternative synthesis of solenopsin and its analogues.

As set forth in FIG. 3, Scheme II, N-boc piperidine is subjected to sec-BuiI at −78° C. followed by dimethylsulfate to provide the methyl substituted N-Boc piperidine analog. The N-Boc piperidine analog prepared above is then subjected to sec-BuLi at −78° C. followed by dimethyl formamide to produce the formyl piperidine derivative which can be further reacted using a Wittig procedure to produce longer chain alkylated products (saturated or unsaturated, as indicated in Scheme II). If one desires an unsaturated side chain, the Wittig reaction may afford such a substituent directly, followed by removal of the Boc group using procedures. Salt formation may also readily occur, using standard methods available in the art and as otherwise described in the examples which follow.

Alternatively, the provide the alkyl (ssaturated) side chains, the Wittig product is reduced using hydrogen/Pd/C to provide the fully saturated side chain. The Boc group may be readily removed using the previously described method, followed by salt formation.

The above-described methods of chemical synthesis may be readily adapted by those of ordinary skill to substitute different sidechains at the 2 and 6 position of the piperidine ring to produce the compounds according to the present invention. These methods may be readily adapted to produce a large number of side chains according to the present invention.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Experimental Data

General Procedures

Analytical thin-layer chromatography (TLC) was performed on Whatman silica gel plates with a UV indicator. Visualization was accomplished by PMA, vanillin, or UV light (254 nm). All reactions were run under an atmosphere of nitrogen and monitored by TLC analysis until the starting material was completely consumed. Unless otherwise indicated, all ethereal workups consisted of the following procedure: the reaction was quenched at room temperature with water. The organic solvent was removed under reduced pressure on a rotary evaporator and the residue was taken up in ether, washed with brine and dried over anhydrous $NaSO_4$. Filtration, followed by concentration under reduced pressure on a rotary evaporator afforded a crude residue which was purified by flash chromatography using silica gel 60 (230–400 mesh) and reagent grade solvents (hexanes, ethyl acetate, ether). Microanalysis was performed by Atlantic Microlab, Inc., Atlanta, Ga. All spectra were obtained in $CDCl_3$. Proton NMR spectra were calibrated using trace $CHCl_3$ as an internal reference.

LAH Reduction of L-Alanine to Give the Corresponding Alcohol (38)

Lithium aluminum hydride (12.78 g, 336.7 mmol) was suspended in anhydrous THF (550 mL) at 0° C. To this mixture was added L-alanine (15.0 g, 168.4 mmol) in portions over a 20 min period. The mixture was then refluxed for 10 h. To the cooled reaction mixture (0° C.) was added 2.0 M NaOH (70 mL). After stirring at room temperature for 3 h, the mixture was filtered and the solids were washed with THF (200 mL). The solids were suspeneded in THF (250 mL), and the resulting mixture was refluxed for 1 h. The solution was filtered and the solids were washed with THF (100 mL). This procedure was repeated twice. The crude alcohol was never isolated, and was used immediately in the next step.

Cbz Protection of the Crude Alcohol to Give the Corresponding N-Cbz Protected derivative (39)

To the combined THF solutions obtained in the previous procedure was added 2.0 M NaOH (168 mL) and benzyl chlorformate (30.2 g, 176.8 mmol). After stirring for 1 h, the biphasic system was separated and the aqueous phase extracted with ethyl acetate (50 mL). The combined organic extracts were dried with $MgSO_4$, filtered and the solvent removed by evaporation to give the N-crude alcohol. This material was purified by recrystallization from THF/cyclohexane to afford the pure alcohol as white needles. mp 79.2–82.7° C. $^1$H NMR (250 MHz) δ7.34–7.21 (m, 5 H), 5.22–5.19 (br s, 1 H), 5.05 (s, 2 H), 3.79–3.74 (m, 1 H), 3.57–3.53 (m, 1 H), 3.48–3.45 (m, 1 H), 3.10–3.08 (br s, 1 H), 1.12–1.09 (d, 3 H); FT-IR (neat) 3453, 3036, 1715, 1517, 1458, 1330, 1266, 1242, 1092, 1032, 696 cm$^{-1}$; MS, m/z 191, 178, 134, 108, 107,91, 79,51, 44,42, 31,27.

Formation of Tosylate (40)

To a stirred solution of compound obtained above, (10.0 g, 47.79 mmol) in 15 mL of pyridine at 0° C. was added p-toluenesulfonyl chloride (9.38, 49.22 mmol). The mixture was allowed to warm to room temperature. After stirring 12 h, ether (50 ml) was added, and the mixture was filtered followed by washing of the solids with additional ether. The combined organic extracts were washed with 0.5N $H_2SO_4$ (3×20 mL), 5% aqueous $NaHCO_3$ (20 mL), saturated brine, and dried with $MgSO_4$. Evaporation of the solvent in vacuo afforded the crude tosylate (13.10 g,75%). Recrystallization was accomplished with THF/hexanes to give the product as white needles. mp 66.2–69.0° C. $^1$H NMR (250 MHz) δ7.76–7.74 (d, 2 H), 7.34–7.27 (m, 7 H), 5.07–4.99 (m, 2 H), 4.86–4.84 (br s, 1 H), 4.01–3.95 (m, 3 H), 2.40 (s, 3 H), 1.12–1.16 (d, 2 H); FT-IR (neat) 3453, 3026, 1722, 1512, 1456, 1358, 1262, 1209, 1180, 976, 830, 697, 662 cm$^{-1}$. MS, m/z 363, 262, 178, 156, 134, 108, 91, 79, 65, 39, 28.

Displacement of Tosylate to Give Iodocarbamate (32)

To a stirred solution of the tosylate obtained above (9.61 g, 26.4 mmol) in 100 mL of acetone at 0° C. was added solid NaI (37.0 g, 264 mmol). After 30 min, the reaction was allowed to warm to room temperature and stirring was continued for 48 h. The solvent was then removed by evaporation. The resulting orange solid was suspended in ethyl acetate (150 mL). This mixture was filtered, and the solids were washed with additional ethyl acetate (100 mL). The organic solution was washed with water, 5% $Na_2S_2O_3$, and saturated brine. The resulting clear solution was dried with $Na_2SO_4$. Filtration and removal of the solvent by evaporation gave the crude iodide (iodocaramate). The material was purified by recrystallization from THF/hexanes to afford the pure product (80%) as white needles. mp 75.8–77.5° C. $^1$H NMR (250 MHz) δ7.38–7.32 (m, 5 H), 5.09–5.06 (m, 1 H), 4.84–4.82 (br s, 1 H), 3.59–2.55 (m, 1 H), 3.41–3.39 (m, 1 H), 3.29–3.26 (m, 1 H), 1.24–1.22 (d, 3 H); ); FT-IR (neat) 3451, 3038, 2980, 1727, 1553, 1513, 1455, 1404, 1327, 1231, 1211, 1100, 1019, 953, 657 cm$^{-1}$. MS, m/z 319, 169, 127, 108, 92, 79, 65, 50, 41, 28.

4-Chloro-1-(phenoxycarbonyl)-2-n-undecyl-1,2-dihydropyridine

To a stirred mixture of magnesium turnings (0.584, 24 mmol) in 40 ml of anhydrous diethyl ether was added 1-bromoundecane (5.36 mL, 24 mmol). After a self sustained reflux period of 10 minutes, the solution was refluxed an additional 45 min and then allowed to cool to room temperature. The newly formed Grignard was canulated in a stirred solution of 4-chloropyridine hydrochloride (1.5 g, 10 mmol) in 80 ml of THF at −78° C. After 20 minutes, phenyl chloroformate (1.26 ml, 10 mmol) was added dropwise. Stirring was continued for 30 min. longer at −78° C. The cooling bath was removed and the reaction mixture was allowed to stir for 30 minutes longer while slowly warming to room temperature. 20% $NH_4Cl$ (30 ml) and ether (40 ml) were added and the layers separated, and the aqueous layer was extracted with two 25 ml portions of ether. The combined organic extracts were washed successively with 25 ml portions of saturated $CuSO_4$, water, saturated $NaHCO_3$, and brine. The organic phase was dried with $MgSO_4$, the solvent was evaporated, to yield the crude product as a yellow oil. Purification by column chromatography with 5% EtOAc in hexanes afforded 3.4 g (88%) of the product as a clear oil which was homogeneous by TLC analysis. $^1$H NMR (300 MHz) δ7.45–7.10 (m, 5 H), 6.94–6.86 (pair of d, 1H), 5.68 (d, 1 H), 5.41–5.29 (dd, 1 H), 5.02–4.85 (m, 1 H), 1.83–1.40 (m, 2 H), 1.24 (br s, 18 H), 0.88 (t, 3H); FT-IR (neat) 2954, 2923, 2852, 1735, 1635, 1592, 1495, 1471, 1332, 1202, 1050 cm$^{-1}$.

1-(tert-Butoxycarbonyl)-4-chloro-2-n-undecyl-1,2-dihydropyridine

To a stirred solution of the 4-Chioro-1-(phenoxycarbonyl)-2-n-undecyl-1,2-dihydropyridine (5.31 g, 13.62 mmol) in 157 ml of THF at −42° C. was added dropwise over 15 minutes a 1.0M solution of potassium t-butoxide (54.5 ml, 54.5 mmol). The resulting orange solution was stirred for 1 h at −42° C. The cooling bath was removed, and the reaction mixture was allowed to stir for 20 min while being slowly warmed to room temperature. Water (40 ml) and ether (80 ml) were added and the aqueous phase was extracted twice with ether. The combined organic extracts were washed with cold 1.0 N NaOH (2×35 ml), and brine. The organic phase was dried over $MgSO_4$, filtered through Celite, and concentrated by evaporation to give the crude product. Column chromatography with 5% EtOAc in hexanes afforded 3.5 g (83%) of the product as a colorless oil which was homogeneous by TLC analysis. $^1$H NMR (300 MHz) d 6.92–6.61 (pair of br d, 1 H), 5.53 (pair of br d, 1 H), 5.55 (br s, 1 H), 5.25–5.11 (pair of br d, 1 H), 4.82–4.63 (br m, 1 H), 1.53 (s, 9 H), 1.24 (br s, 20 H), 0.83 (t, 3H); $^{13}$C NMR (75 MHz) 152.6 (s), 151.8 (s), 127.7 (s), 127.5 (s), 117.8 (s), 117.4 (s), 106.6 (s), 106.2 (s), 8.17 (s), 54.1 (s), 53.2 (s), 34.3 (s), 33.8 (s), 31.9 (s), 29.7 (s), 29.6 (s), 29.5 (s), 29.3 (s), 2.81 (s), 24.3 (s), 22.7 (s), 14.1 (s) ppm; FT-IR 2954, 2926, 2855, 1717, 1633, 1369, 1390, 1171, 1145, 1129, 1054 cm$^{-1}$.

1-(tert-Butoxycarbonyl)-4-chloro-6-methyl-2-n-undecyl-1,2-dihydropyridine

To a stirred solution of 1-(tert-Butoxycarbonyl)-4-chloro-2-n-undecyl-1,2-dihydropyridine (3.15, 8.51 mmol) in 115 ml of THF at −42° C. was added n-butyllithium (6.4 mL, 10.2 mmol, 1.6 M solution in hexanes) dropwise via syringe. After the mixture had stirred at −42° C. for 1 h, iodomethane (1.6 mL, 25.54 mmol) was added and stirring was continued at −42° C. for 1 h and then at room temperature for 1 h. Water (30 mL) and ether (60 mL) were added, the layers were separated, the aqueous phase was extracted with ether (2×15 mL), and the combined organic extracts were washed with brine. The organic phase was dried over $K_2CO_3$ filtered through silica gel/Celite, and concentrated in vacuo to give the crude product. Purification by column chromatography gave with 5% EtOAc in hexanes afforded 2.5 g (77%) of the product as a clear orange oil which was homogeneous by TLC analysis. $^1$H NMR (250 MHz) d 5.62 (dd, 1 H), 5.30 (m, 1 H), 4.76 (dt 1 H), 2.16 (s, 3 H), 1.53 (s, 9 H), 1.48–1.40 (m, 2 H), 1.26 (br s, 18 H), 0.84 (t, 3 H); $^{13}$C NMR (62.7 MHz) 153.1 (s), 137.1 (s), 126.6 (s), 119.4 (s), 112.3 (s), 81.4 (s), 54.2 (s), 31.9 (s), 31.8 (s), 29.69 (s), 29.63 (s), 29.55 (s), 29.44 (s), 29.36 (s), 29.33 (s), 28.2 (s), 24.6 (s), 22.7 (s), 22.0 (s), 14.1 (s) ppm. FT-IR (neat) 2956, 2924, 2852, 1709, 1637, 1471, 1393, 1368, 1342, 1169, 1131 cm$^{-1}$.

1-(tert-Butoxycarbonyl)-6-methyl-2-n-undecyl-1,2,3,4-tetrahydropyridine

To a stirred solution of 2.17g, (5.65 mmol) of 1-(tert-Butoxycarbonyl)-4-chloro-6-methyl-2-n-undecyl-1,2-dihydropyridine in 120 mL of MeOH at 0° C. was added 0.422 g (5.71 mmol) of lithium carbonate followed by of 5% Pd/C. The flask was evacuated and filled with hydrogen repeatedly. The system was placed under positive pressure from a balloon, and the reaction was monitored by removing aliquots with a syringe, concentrating the aliquot in vacuo, and examing its $^1$H NMR spectrum. Upon completion, the mixture was filtered through Celite, and concentrated by evaporation. The residue was dissolved in ether (20 mL), water(20 mL) was added, and the aqueous phase was extracted twice with ether(2×10 mL). The combined organic extracts were washed with 1M NaOH(2×20ml) and brine. The organic products were dried over K$_2$CO$_3$, filtered through Celite, and concentrated in vacuo to give the crude product. Purification by column chromatography, (silica gel, 10% ether in hexanes) afforded 1.35 g (70%) the product as a light yellow oil which was homogeneous by TLC analysis. $^1$H NMR (300 MHz) δ4.75 (br s, 1 H), 4.62 (m, 1 H), 2.21 (s, 3 H), 1.91–1.64 (m, 4 H), 1.52 (s, 9 H), 1.28 (br s, 20 H), 0.90 (t, 3H); $^{13}$C NMR (75 MHz) 154.1 (s), 133.5 (s), 110.4 (s), 79.6 (s), 52.1 (s), 32.3 (s), 30.1 (s), 30.0 (s), 29.9 (s), 28.5 (s), 26.7 (s), 23.5 (s), 23.2 (s), 19.8 (s), 14.4 (s) ppm. FT-IR (neat) 2928, 2860, 1694, 1457, 1368, 1352, 1168, 1124, 1095, 1073 cm$^{-1}$.

trans-N-Boc-2-methyl-6-n-undecylpiperidine

To a stirred solution of 1.34 g (3.81 mmol) of 1-(tert-Butoxycarbonyl)-6-methyl-2-n-undecyl-1,2,3,4-tetrahydropyridine in 260 mL of CH$_2$Cl$_2$ was added 1.44 g (22.86 mmol) of sodium cyanoborohydride. After being stirred 15 minutes at room temperature, the heterogeneous solution was cooled to −42° C. and TFA (3.7 mL, 38.10 mmol) was added slowly dropwise. After being stirred for 4 h at −42° C., the cold bath was removed, and the reaction mixture was immediately quenched with 190 mL of a saturated aqueous NaHCO$_3$/THF mixture (50:50). The aqueous phase was extracted with CH$_2$Cl$_2$ (2×40 mL) and the combined organic extracts were washed with water and brine. The organic phase was dried with K$_2$CO$_3$, filtered through Celite, and evaporated to give the crude product. Column chromatography using 5% EtOAc in hexanes gave 0.9 g (67%) of the product as a clear colorless oil. $^1$H NMR (300 MHz) d 3.97–3.84 (m, 1 H), 3.83–3.74 (m, 1 H), 1.92–1.28 (m, 8 H), 1.46 (s, 9 H), 1.25 (br s, 18 H), 1.22 (d, 3 H), 0.89 (t, 3 H); $^{13}$C NMR (75 MHz) 155.3 (s), 78.7 (s), 51.6 (s), 46.9 (s), 34.3 (s), 31.7 (s), 29.6 (s), 29.5 (s), 29.3 (s), 28.4 (s), 27.2 (s), 26.8 (s), 23.2 (s), 22.7 (s), 20.8 (s), 14.0 (s), 13.6 (s) ppm. FT-IR (neat) 2924, 2854, 2691, 1468, 1394, 1368, 1178, 1091 cm$^{-1}$.

(±)-Solenopsin A*HCl. trans-2-methyl-6-n-undecylpiperidine hydrochloride

To a stirred solution of 0.463 g of trans-N-Boc-2-methyl-6-n-undecylpiperidine in 50 ml of CH$_2$Cl$_2$ at 0° C. was added dropwise 12.2 mL (excess) of trifluoroacetic acid. The cooling bath was removed, and stirring was continued for 1 h at room temperature. After concentrating the resulting solution on a rotary evaporator, the remaining liquid was dissolved in ether (50 mL), and 25 ml of water was added. The aqueous phase was extracted with ether (2*40 mL), and the combined organic extracts were washed with saturated NaHCO$_3$ (2*40 mL) and brine. The organic phase was dried over K$_2$CO$_3$, filtered through Celite, and concentrated in vacuo to give an oil. The crude product was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as white needles. $^1$H NMR (300 MHz) δ9.30 (br s, 2 H), 3.53 (br s, 1 H), 3.27 (br s, 1 H), 1.96–1.22 (m, 29 H), 0.85 (t, 3 H); $^{13}$C NMR (75 MHz) 52.0 (s), 48.2 (s), 32.1 (s), 31.0 (s), 29.8 (s), 29.75 (s), 29.7 (s), 29.6 (s), 2.95 (s), 29.2 (s), 26.5 (s), 26.1 (s), 22.9 (s), 17.6 (s), 17.1 (s), 14.3 (s) ppm. FT-IR (neat) 3420, 2931, 2853, 1465, 1376, 1141, 1067 cm$^{-1}$.

4-Chloro-1-(phenoxycarbonyl)-2-n-pentyl-1,2-dihydropyridine

To a stirred mixture of 4-chloropyridine hydrochloride (3 g, 20 mmol) in 200 mL of THF at −78° C. was added 24 mL (48 mmol) of pentylmagnesium bromide (2M soln in ether) slowly dropwise. After being stirred at −78° C. for 20 minutes, phenyl chloroformate (2.51 mL, 20 mmol) was added and the mixture was stirred for 30 minutes at −78° C. The cooling bath was removed and the reaction mixture was allowed to stir while slowly warming to room temperature. Aqueous 20% NH$_4$Cl (50 mL) and ether (80 mL) were added, the layers were separated, and the queous phase was extracted twice with ether. The combined organic extracts were washed successively with 50 mL portions of saturated aqueous CuSO$_4$, water, saturated NaHCO$_3$, and brine. The organic phase was dried over MgSO$_4$, filtered through Celite, and evaporated to give 6.2 g (quantitative) of the crude product. This crude material was used directly in the next step to make the N-Boc derivative. $^1$H NMR (250 MHz) d 7.45–7.05 (m, 5 H), 5.68 (d, 1 H), 5.33 (m, 1 H), 4.92 (m, 1 H), 1.9–1.1 (m, 8 H), 0.87 (t, 3 H).

1-(tert-Butoxycarbonyl)4-chloro-2-n-pentyl-1,2-dihydropyridine

To a stirred solution of 4-Chloro-1-(phenoxycarbonyl)-2-n-pentyl-1,2-dihydropyridine (7.1 g, 23.22 mmol) in 250 ml of THF at −42° C. was added dropwise over 15 minutes a 1.0M solution of potassium t-butoxide (93 mL, 92.87 mmol). The resulting orange solution was stirred for 1 h at −42° C. The cooling bath was removed, and the reaction mixture was allowed to stir for 20 min while being slowly warmed to room temperature. Water (50 ml) and ether (70 ml) were added and the aqueous phase was extracted twice with ether. The combined organic extracts were washed with cold 1.0 N NaOH (2×35 ml), and brine. The organic phase was dried over MgSO$_4$, filtered through Celite, and concentrated in vacuo to give the crude product. Column chromatography with 5% EtOAc in hexanes afforded 4.78 (73%) of the product. $^1$H NMR (250 MHz) d 6.85–6.70 (dd, 1 H), 5.54 (br s, 1 H), 5.19–4.91 (m, 1 H), 4.72–4.51 (m, 1 H), 1.69–1.26 (m, 17 H), 0.89–0.84 (t, 3 H); $^{13}$C NMR (62.7 MHz) 151.8 (s), 127.5–126 (d), 117.8–117.4 (d), 106.6–106.1 (d), 81.7 (s), 54.0 (s), 53.1 (s), 34.1 (s), 33.6 (s), 31.6 (s), 28.1 (s), 23.9 (s), 22.6 (s), 14.0 (s) ppm.

1-(tert-Butoxycarbonyl)-4-chloro-6-methyl-2-n-pentyl-1,2-dihydropyridine

To a stirred solution of 1-(tert-Butoxycarbonyl)-4-chloro-2-n-pentyl-1,2-dihydropyridine (4.67 g, 16.33 mmol) in 170 ml of THF at −42° C. was added n-butyllithium (7.84 mL, 19.61 mmol) dropwise via syringe. After the mixture had stirred at −42° C. for 1 h, iodomethane (3.1 mL, 48.99 mmol) was added and stirring was continued at −42° C. for 1 h and then at room temperature for 1 h. Water (50 mL) and ether (100 mL) were added, the layers were separated, the aqueous phase was extracted with ether (2×15 mL), and the combined organic extracts were washed with brine. The organic phase was dried over $K_2CO_3$ filtered through silica gel/Celite, and concentrated in vacuo to give the crude product. Purification by column chromatography with 5% EtOAc in hexanes afforded 3.6 g (74%) of the product. $^1$H NMR (250 MHz) d 5.62–5.59 (d, 1 H), 5.31 (br s, 1 H), 4.80–4.72 (q, 1 H), 2.13 (s, 1 H), 1.55–1.26 (m, 17 H), 0.89–0.84 (t, 3 H); $^{13}$C NMR (62.7 MHz) 153.0 (s), 136.9 (s), 126.5 (s), 119.3 (s), 112.2 (s), 81.4 (s), 54.1 (s), 31.6 (s), 31.5 (s), 28.1 (s), 24.2 (s), 22.4 (s), 21.9 (s), 13.9 (s), ppm. FT-IR (neat) 2927, 2855, 1706, 1634, 1391, 1128, 1087 cm$^{-1}$.

1-(tert-Butoxycarbonyl)-6-methyl-2-n-pentyl-1,2,3,4-tetrahydropyridine

To a stirred solution of 1-(tert-Butoxycarbonyl)-4-chloro-6-methyl-2-n-pentyl-1,2-dihydropyridine (3.48 g, 11.61 mmol) in 220 mL of MeOH at 0° C. was added of lithium carbonate 0.857 g, 11.61 mmol) followed by 5% Pd/C. The mixture was placed under a positive pressure of hydrogen gas from a balloon, and the reaction progress was monitored by removing aliquots with a syringe, concentrating the aliquot in vacuo, and examining its $^1$H NMR spectrum. Upon completion, the mixture was filtered through Celite and evaporated. The residue was dissolved in ether (100 mL) and water (50 mL) was added, and the aqueous phase was extracted twice with ether. The combined organic extracts were washed with 1M NaOH and brine. The organic phase was dried with potassium carbonate, filtered through Celite, and concentrated in vacuo to give the crude product. Purification by column chromatography (silica gel, 5% EtOAc in hexanes) afforded 3.04 g (98%) of the product which was homogeneous by TLC analysis. $^1$H NMR (300 MHz) d 4.86 (br s, 1 H), 4.39–4.31 (m, 1 H), 2.02 (s, 3 H), 1.98–1.92 (m, 2 H), 1.91–1.28 (m, 21 H), 0.9–0.85 (t, 3 H); $^{13}$C NMR (75 MHz) 153.8 (s), 132.5 (s), 110.9 (s), 79.9 (s), 51.9 (s), 31.7 (s), 29.4 (s), 28.3 (s), 26.0 (s), 25.8 (s), 23.1 (s), 22.6 (s), 19.5 (s), 13.9 (s) ppm. FT-IR (neat) 2956, 2927, 2856, 1693, 1658, 1454, 1349, 1253, 1169, 1124, 1072 cm$^{-1}$.

trans-N-Boc-2-methyl-6-n-pentylpiperidine

To a stirred solution of 1-(tert-Butoxycarbonyl)-6-methyl-2-n-pentyl-1,2,3,4-tetrahydropyridine (1.0 g, 3.74 mmol) in 250 mL of $CH_2Cl_2$ was added sodium cyanoborohydride (1.41 g, 22.43 mmol). After being stirred 15 minutes at room temperature, the heterogeneous solution was cooled to −42° C. and TFA (2.9 mL, 37.4 mmol) was added slowly dropwise. After being stirred for 4 h at −42° C., the cold bath was removed, and the reaction mixture was immediately quenched with 200 mL of a saturated aqueous $NaHCO_3$/THF mixture (50:50). The aqueous phase was extracted with $CH_2Cl_2$ (2×70 mL) and the combined organic extracts were washed with water and brine. The organic phase was dried with $K_2CO_3$, filtered through Celite, and evaporated to give crude product. Column chromatography using 5% EtOAc in hexanes gave 0.8 g (70%) of the product which was homogeneous by TLC analysis. $^1$H NMR (300 MHz) d 3.92–3.81 (m, 1 H), 3.69–3.80 (m, 1 H), 1.91–1.21 (m, 26 H), 0.90–0.86 (t, 3 H).

trans-2-methyl-6-n-pentylpiperidine hydrochloride

To a stirred solution of trans-N-Boc-2-methyl-6-n-pentylpiperidine (0.77 g. 2.86 mmol) in 90 ml of $CH_2Cl_2$ at 0° C. was ad dropwise trifluoroacetic acid (6.6 mL, 85.72 mmol). The cooling bath was removed, and stirring was continued for 1 h at room temperature. After concentrating the resulting solution on a rotary evaporator, the remaining liquid was dissolved in ether (40 mL), and 20 ml of water was added. The aqueous phase was extracted with ether (2*10 mL), and the combined organic extracts were washed with saturated $NaHCO_3$ (2*30 mL) and brine. The organic phase was dried over $K_2CO_3$, filtered through Celite, and concentrated on a rotary evaporator. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as white needles. mp 109.6–110.9° C.; $^1$H NMR (300 MHz) δ9.30 (br s, 2 H), 3.53 (br. s, 1 H), 3.27 (br s, 1 H), 1.96–1.29 (m, 17 H), 0.89–0.85 (t, 3 H); $^{13}$C NMR (75 MHz) 51.7 (s), 47.9 (s), 31.4 (s), 30.6 (s), 28.8 (s), 28.1 (s), 26.1 (s), 25.4 (s), 24.9 (s), 22.4 (s), 17.3 (s), 16.8 (s). FT-IR: 3421, 2932, 1589, 1458, 1392, 1378, 1357, 1102, 727. Elemental Analysis for $C_{11}H_{24}NCl$: C, 64.21%; H, 11.76%; N, 6.81%. Found: C, 64.19%; H, 11.72%; N, 6.71%.

4-Chloro-1-(phenoxycarbonyl)-2-n-hexyl-1,2-dihydropyridine

To a stirred mixture of 4-chloropyridine hydrochloride (3 g, 20 mmol) in 200 mL of THF at −78° C. was added 24 mL (48 mmol) of pentylmagnesium bromide (2M soln in ether) slowly dropwise. After being stirred at −78° C. for 20 minutes, phenyl chloroformate (2.51 mL, 20 mmol) was added and the mixture was stirred for 30 minutes at −78° C. The cooling bath was removed and the reaction mixture was allowed to stir while slowly warming to room temperature. Aqueous 20% $NH_4Cl$ (50 mL) and ether (80 mL) were added, the layers were separated, and the queous phase was extracted twice with ether. The combined organic extracts were washed successively with 50 mL portions of saturated aqueous $CuSO_4$, water, saturated $NaHCO_3$, and brine. The organic phase was dried over $MgSO_4$, filtered through Celite, and evaporated to give 6.4 g (quantitative) of the crude product. This crude material was used directly in the next step to make the N-Boc derivative. $^1$H NMR (250 MHz) δ7.52–6.99 (m, 5 H), 5.63 (d, 1 H), 5.24 (m, 1 H), 4.95 (m, 1 H), 1.93–1.16 (m, 8 H), 0.87 (t, 3 H).

1-(tert-Butoxycarbonyl)-4-chloro-2-n-hexyl-1,2-dihydropyridine

To a stirred solution of 4-Chloro-1-(phenoxycarbonyl)-2-n-hexyl-1,2-dihydropyridine (7.42 g, 23.2 mmol) in 250 ml of THF at −42° C. was added dropwise over 15 minutes a 1.0M solution of potassium t-butoxide (93 mL, 92.87 mmol). The resulting orange solution was stirred for 1 h at −42° C. The cooling bath was removed, and the reaction mixture was allowed to stir for 20 min while being slowly warmed to room temperature. Water (50 ml) and ether (70 ml) were added and the aqueous phase was extracted twice with ether. The combined organic extracts were washed with cold 1.0 N NaOH (2×35 ml), and brine. The organic phase was dried over $MgSO_4$, filtered through Celite, and concentrated in vacuo to give the crude product. Column chromatography with 5% EtOAc in hexanes afforded 5.9 g (81% from previous reaction) as a clear colorless oil that was homogeneous by TLC analysis. $^1$H NMR (250 MHz)

δ 6.85–6.63 (dd, 1 H), 5.55 (br s, 1 H), 5.23–5.12 (m, 1 H), 4.87–4.56 (m, 1 H), 1.72–1.25 (m, 19 H), 0.89–0.85 (t, 3 H).

1-(tert-Butoxycarbonyl)-4-chloro-6-methyl-2-n-hexyl-1,2-dihydropyridine

To a stirred solution of 1-(tert-Butoxycarbonyl)-4-chloro-2-n-hexyl-1,2-dihydropyridine (4.84 g, 16.14 mmol) in 180 ml of THF at −42° C. was added n-butyllithium (19.4 mL, 19.37 mmol) dropwise via syringe. After the mixture had stirred at −42° C. for 1 h, iodomethane (3.0 mL, 48.42 mmol) was added and stirring was continued at −42° C. for 1 h and then at room temperature for 1 h. Water (50 mL) and ether (100 mL) were added, the layers were separated, the aqueous phase was extracted with ether (2×15 mL), and the combined organic extracts were washed with brine. The organic phase was dried over $K_2CO_3$ filtered through silica gel/Celite, and concentrated in vacuo to give the crude product. Purification by column chromatography with 5% EtOAc in hexanes afforded 4.89 g (73.4%) of the product as an orange oil that was homogeneous by TLC analysis. $^1$H NMR (250 MHz) δ5.65–5.58 (d, 1 H), 5.32 (br s, 1 H), 4.84–4.72 (q, 1 H), 2.13 (s, 3 H), 1.75–1.21 (m, 19 H), 0.91–0.85 (t, 3 H).

1-(tert-Butoxycarbonyl)-6-methyl-2-n-pentyl-1,2,3,4-tetrahydropyridine

To a stirred solution of 1-(tert-Butoxycarbonyl)-4-chloro-6-methyl-2-n-hexyl-1,2-dihydropyridine (3.74 g, 11.91 mmol) in 250 mL of MeOH at 0° C. was added of lithium carbonate (0.88 g, 11.91 mmol) followed by 5% Pd/C. The mixture was placed under a positive pressure of hydrogen gas from a balloon, and the reaction progress was monitored by removing aliquots with a syringe, concentrating the aliquot in vacuo, and examining its $^1$H NMR spectrum. Upon completion, the mixture was filtered through Celite and evaporated. The residue was dissolved in ether (100 mL) and water (50 mL) was added, and the aqueous phase was extracted twice with ether. The combined organic extracts were washed with 1M NaOH and brine. The organic phase was dried with potassium carbonate, filtered through Celite, and concentrated in vacuo to give the crude product. Purification by column chromatography (silica gel, 5% EtOAc in hexanes) afforded 2.09 g (62%) as a clear oil that was homogeneous by TLC analysis. $^1$H NMR (300 MHz) δ4.85 (br s, 1 H), 4.43–4.38 (m, 1 H), 2.01 (s, 3 H), 1.99–1.91 (m, 2 H), 1.83–1.12 (m, 23 H), 0.89–0.84 (t, 3 H).

trans-N-Boc-2-methyl-6-n-hexylpiperidine

To a stirred solution of 1-(tert-Butoxycarbonyl)-6-methyl-2-n-pentyl-1,2,3,4-tetrahydropyridine (1.0 g, 3.55 mmol) in 240 mL of $CH_2Cl_2$ was added sodium cyanoborohydride (1.34 g, 21.3 mmol). After being stirred 15 minutes at room temperature, the heterogeneous solution was cooled to −42° C. and TFA (3.5 mL, 35.53 mmol) was added slowly dropwise. After being stirred for 4 h at −42° C., the cold bath was removed, and the reaction mixture was immediately quenched with 200 mL of a saturated aqueous $NaHCO_3$/THF mixture (50:50). The aqueous phase was extracted with $CH_2Cl_2$ (2×70 mL) and the combined organic extracts were washed with water and brine. The organic phase was dried with $K_2CO_3$, filtered through Celite, and evaporated to give crude product. Column chromatography using 5% EtOAc in hexanes gave 0.54 g (54%) of the product which was homogeneous by TLC analysis. $^1$H NMR (300 MHz) δ3.99–3.82 (m, 1 H), 3.79–3.74 (m, 1 H), 1.91–1.15 (m, 28 H), 0.92–0.83 (t, 3 H); $^{13}$C NMR (75 Mhz) 155.6 (s), 78.6 (s), 51.6 (s), 46.9 (s) 34.34 (s), 31.9 (s), 29.3 (s), 28.5 (s), 27.1 (s), 26.9 (s), 2.31 (s), 22.6 (s), 20.8 (s), 14.0 (s), 13.7 (s) ppm.

trans-2-methyl-6-n-hexylpiperidine hydrochloride

To a stirred solution of trans-N-Boc-2-methyl-6-n-hexylpiperidine (1.14 g. 4.02 mmol) in 90 ml of $CH_2Cl_2$ at 0° C. was added dropwise trifluoroacetic acid (6.6 mL, 85.72 mmol). The cooling bath was removed, and stirring was continued for 1 h at room temperature. After concentrating the resulting solution on a rotary evaporator, the remaining liquid was dissolved in ether (40 mL), and 20 ml of water was added. The aqueous phase was extracted with ether (2*10 mL), and the combined organic extracts were washed with saturated $NaHCO_3$ (2*30 mL) and brine. The organic phase was dried over $K_2CO_3$, filtered through Celite, and concentrated on a rotary evaporator. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give 0.74 g (48%) of the piperidinium hydrochloride as white needles. mp 130.7–131.8° C.; $^1$H NMR (300 MHz) δ9.32 (s, 2H), 3.53 (s, 1H), 3.27 (s, 1H), 2.01–1.26 (m, 19 H), 0.85 (t, 3H); $^{13}$C NMR (75 MHz) δ51.7 (s), 47.9 (s), 31.6 (s), 30.7 (s), 28.92 (s), 28.84 (s), 26.11 (s), 25.72 (s), 22.48 (s), 17.29 (s), 16.83 (s), 13.97 (s). FT-IR: 3489, 2934, 1558, 1540, 1473, 1457, 1299, 1123, 1072, 977, 885, 721. Elemental Analysis for $C_{12}H_{26}NCl$: C, 65.58%; H, 11.92%; N, 6.37%. Found: C, 65.60%; H, 11.86%; N, 6.27%.

4-Chloro-1-(phenoxycarbonyl)-2-cyclopentyl-1,2-dihydropyridine

To a stirred mixture of 4-chloropyridine hydrochloride (3 g, 20 mmol) in 200 mL of THF at −78° C. was added 24 mL (48 mmol) of pentylmagnesium bromide (2M soln in ether) slowly dropwise. After being stirred at −78° C. for 20 minutes, phenyl chloroformate (2.51 mL, 20 mmol) was added and the mixture was stirred for 30 minutes at −78° C. The cooling bath was removed and the reaction mixture was allowed to stir while slowly warming to room temperature. Aqueous 20% $NH_4Cl$ (50 mL) and ether (80 mL) were added, the layers were separated, and the queous phase was extracted twice with ether. The combined organic extracts were washed successively with 50 mL portions of saturated aqueous $CuSO_4$, water, saturated $NaHCO_3$, and brine. The organic phase was dried over $MgSO_4$, filtered through Celite, and evaporated to give the crude product. Purification by column chromatography (silica gel, 5% EtOAc in hexanes) afforded 5.25 g (86.4%) of the product as a yellow oil that was homogeneous by TLC analysis. $^1$H NMR (250 MHz) δ7.61–5.67 (m, 5 H), 5.66 (d, 1 H), 5.28 (m, 1 H), 5.01 (m, 1 H), 2.21 (m, 1 H), 1.98–1.28 (m, 8 H).

1-(tert-Butoxycarbonyl)4-chloro-2-cyclopentyl-1,2-dihydropyridine

To a stirred solution of 4-Chloro-1-(phenoxycarbonyl)-2-cyclopentyl-1,2-dihydropyridine (5.52 g, 17.3 mmol) in 200 ml of THF at −42° C. was added dropwise over 15 minutes a 1.0M solution of potassium t-butoxide (50 mL, 50 mmol). The resulting orange solution was stirred for 1 h at −42° C. The cooling bath was removed, and the reaction mixture was allowed to stir for 20 min while being slowly warmed to room temperature. Water (50 ml) and ether (70 ml) were added and the aqueous phase was extracted twice with ether. The combined organic extracts were washed with cold 1.0 N NaOH (2×35 ml), and brine. The organic phase was dried over $MgSO_4$, filtered through Celite, and concentrated in vacuo to give the crude product. Column chromatography with 5% EtOAc in hexanes afforded 3.71 g (75.7%) of the product which was homogeneous by TLC analysis. $^1$H NMR (250 MHz) δ6.89–6.67 (dd, 1 H), 5.58 (br s, 1 H), 5.27–5.23 (m, 1 H), 4.92–4.62 (m, 1 H), 2.21 (m, 1 H), 1.892–1.25 (m, 17 H).

1-(tert-Butoxycarbonyl)-4-chloro-6-methyl-2-cyclopentyl-1,2-dihydropyridine

To a stirred solution of 1-(tert-Butoxycarbonyl)-4-chloro-2-cyclopentyl-1,2-dihydropyridine (3.69 g, 12.99 mmol) in 180 ml of THF at −42° C. was added n-butyllithium (6.25 mL, 15.59 mmol) dropwise via syringe. After the mixture had stirred at −42° C. for 1 h, iodomethane (2.4 mL, 38.97 mmol) was added and stirring was continued at −42° C. for 1 h and then at room temperature for 1 h. Water (50 mL) and ether (100 mL) were added, the layers were separated, the aqueous phase was extracted with ether (2×15 mL), and the combined organic extracts were washed with brine. The organic phase was dried over $K_2CO_3$ filtered through silica gel/Celite, and concentrated in vacuo to give the crude product. Purification by column chromatography with 5% EtOAc in hexanes afforded 2.60 g (69%) of the product as an orange oil that was homogeneous by TLC analysis. $^1$H NMR (250 MHz) δ5.68–5.61 (d, 1 H), 5.37 (br s, 1 H), 4.86–4.73 (q, 1 H), 2.21 (m, 1 H), 2.14 (s, 3 H), 1.76–1.20 (m, 17 H).

1-(tert-Butoxycarbonyl)-6-methyl-2-cyclopentyl-1,2,3,4-tetrahydropyridine

To a stirred solution of 1-(tert-Butoxycarbonyl)-4-chloro-6-methyl-2-cyclopentyl-1,2-dihydropyridine (2.54 g, 8.53 mmol) in 175 mL of MeOH at 0° C. was added of lithium carbonate (0.63 g, 8.53 mmol) followed by 5% Pd/C. The mixture was placed under a positive pressure of hydrogen gas from a balloon, and the reaction progress was monitored by removing aliquots with a syringe, concentrating the aliquot in vacuo, and examining its $^1$H NMR spectrum. Upon completion, the mixture was filtered through Celite and evaporated. The residue was dissolved in ether (100 mL) and water (50 mL) was added, and the aqueous phase was extracted twice with ether. The combined organic extracts were washed with 1M NaOH and brine. The organic phase was dried with potassium carbonate, filtered through Celite, and concentrated in vacuo to give the crude product. Purification by column chromatography (silica gel, 5% EtOAc in hexanes) afforded 1.14 g (52%) as a clear oil that was homogeneous by TLC analysis. $^1$H NMR (300 MHz) δ4.87 (br s, 1 H), 4.45–4.40 (m, 1 H), 2.22, (m, 1H), 2.02 (s, 3 H), 1.99–1.91 (m, 2 H), 1.82–1.20 (m, 21 H).

trans-N-Boc-2-methyl-6-cyclopentylpiperidine

To a stirred solution 1-(tert-Butoxycarbonyl)-6-methyl-2-cyclopentyl-1,2,3,4-tetrahydropyridine (1.14 g, 4.29 mmol) in 290 mL of $CH_2Cl_2$ was added sodium cyanoborohydride (1.62 g, 25.8 mmol). After being stirred 15 minutes at room temperature, the heterogeneous solution was cooled to −42° C. and TFA (4.9 mL, 42.95 mmol) was added slowly dropwise. After being stirred for 4 h at −42° C., the cold bath was removed, and the reaction mixture was immediately quenched with 200 mL of a saturated aqueous $NaHCO_3$/THF mixture (50:50). The aqueous phase was extracted with $CH_2Cl_2$ (2×70 mL) and the combined organic extracts were washed with water and brine. The organic phase was dried with $K_2CO_3$, filtered through Celite, and evaporated to give crude product. Column chromatography using 5% EtOAc in hexanes gave 1.15 g (73%) of the product which was homogeneous by TLC analysis. $^1$H NMR (300 MHz) 67 4.12–3.91 (m, 1 H), 3.79–3.74 (m, 1 H), 2.21 (m, 1 H), 2.19–1.15 (m, 26 H).

trans-2-methyl-6-cyclopentylpiperidine hydrochloride

To a stirred solution of trans-N-Boc-2-methyl-6-cyclopentylpiperidine (0.84 g. 3.14 mmol) in 115 ml of $CH_2Cl_2$ at 0° C. was added dropwise trifluoroacetic acid (7.3 mL, 94.22 mmol). The cooling bath was removed, and stirring was continued for 1 h at room temperature. After concentrating the resulting solution on a rotary evaporator, the remaining liquid was dissolved in ether (40 mL), and 20 ml of water was added. The aqueous phase was extracted with ether (2*10 mL), and the combined organic extracts were washed with saturated $NaHCO_3$ (2*30 mL) and brine. The organic phase was dried over $K_2CO_3$, filtered through Celite, and concentrated on a rotary evaporator. The crude oil was immediately dissolved in a small amount of ether, and ether saturated with HCl (g) was added slowly via pipette. This solution was allowed to stand for minutes, and the solvent was evaporated. More ether was added and the flask was swirled constantly until crystallization occured. The solid was collected via filtration, and dried in vacuo to give 0.350 g (55%) of the piperidinium hydrochloride as white needles. mp 166.0–166.9° C.; $^1$H NMR (300 MHz) δ9.26–9.0 (br d, 2H), 3.67 (s, 1H), 2.99 (s, 1H), 2.31–1.18 (m, 18H); $^{13}$C NMR (75 MHz) δ52.1 (s), 48.3 (s), 31.5 (s). 28.9 (s), 28.9 (s), 26.9 (s), 25.3 (s), 22.4 (s), 20.8 (s). FT-IR (neat): 3420, 2940, 2867, 1652, 1591, 1456, 1428, 1417, 1176, 1120, 1087, 998, 879. Elemental Analysis for $C_{11}H_{22}NCl$: C, 64.83%; H, 10.90%; N, 6.87%. Found: C, 64.96%; H, 10.94%; N, 6.84%.

N-Boc-Piperidine

A solution of di-tert-butyl dicarbonate (43.7 g, 0.2 mol) in 200 mL of THF was cooled to 0° C. and treated with piperidine (29.7 mL, 0.3 mol) dropwise. The mixture was stirred for 10 min, warmed to room temperature, and then stirred for 30 minutes. The mixture was diluted with of 10% sodium bicarbonate solution and extracted with ether. The extracts were washed with brine, and combined extracts were dried over $K_2CO_3$ and then concentrated to give a crude product as an oil. Purification by distillation under reduced pressure afforded 36.1 g (97%) of product as a clear oil which was homogeneous by TLC analysis. $^1$H NMR (250 MHz) δ3.37–3.33 (br. t, 4 H), 1.56–1.44 (m, 15 H); $^{13}$C NMR (62.7 MHz) 154.8 (s), 78.9 (s), 44.5 (br. s), 28.4 (s), 25.6 (s), 24.4 (s) ppm.

N-Boc-Piperidine-2-Carboxaldehyde

A solution of N-Boc-Piperidine (6.0 g, 32.4 mmol) in ether (65 mL) was cooled to −60° C. and treated with TMEDA (4.9 mL, 32.4 mmol) followed by sec-BuLi (54.8 mL, 71.2 mmol) dropwise. The mixture was slowly warmed to −20° C. and stirred for 10 min and then cooled to −78° C. The mixture was treated with a solution of DMF (3.8 mL, 48.6 mmol) in 6 mL of ether via syringe, stirred for 10 min, and then quenched with 60 mL saturated ammonium chloride solution. The mixture was warmed to room temperature, and the organic layer was separated. The aqueous layer was extracted three times with ether, and the combined extracts were dried over $K_2CO_3$. The organic layer was concentrated to give a crude product as an orange oil. Purification by column chomatography on silica gel with hexanes:EtOAc (4: 1) afforded 4.2 g (67%) of the product as a clear oil which was homogeneous by TLC analysis. $^1$H NMR (300 MHz) δ9.58 (s, 1 H), 4.69–4.51 (br. m, 1 H), 4.12–3.85 (br. m, 1 H), 2.85 (br. s, 1 H), 2.19–2.13 (d, 1 H), 1.72–1.23 (m, 15 H); $^{13}$C NMR (75 MHz) 201.4 (s), 80.4 (s), 43.0 (br. s), 28.3 (s), 24.7 (s), 23.6 (s), 20.9 (s) ppm.

N-Boc-2-Methyl-Piperidine

A solution of N-Boc-Piperidine (15.0 g, 80.95 mmol) in ether (160 mL) was cooled to −78° C. and treated with TMEDA (15.9 mL, 105.2 mmol) followed by sec-BuLi (85 mL, 105.2 mmol) dropwise. The mixture was stirred for 3 h at −78° C. and then treated with a solution of dimethyl sulfate (15.3 mL, 161.9 mmol) in 65 mL of ether. The mixture was warmed to room temperature and then was diluted with water and extracted with ether. The combined extracts were dried over $K_2CO_3$ and then concentrated to give a crude product as a colorless oil. The product was purified by column chromatography on silca gel with 5% EtOAc/hexane to afford 16.0 g (81%) of product as a clear oil which was homogeneous by TLC analysis. $^1$H NMR (300 MHz) 67 4.33 (m, 1 H), 3.92–3.81 (pair of br. d, 1 H), 2.81–2.72 (dt, 1H), 1.60–1.36 (m, 15 H), 1.09–1.07 (d, 3 H); $^{13}$C NMR (75 MHz) 154.9 (s), 78.6 (s), 45.9 (s), 38.6 (s), 29.9 (s), 28.4 (s), 25.6 (s), 18.6 (s), 15.6 (s), ppm.

trans-N-Boc-2-Methyl-6-Piperidinecarboxaldehyde

A solution of N-Boc-2-Methyl-Piperidine (9.4 g, 46.9 mmol) in 94 mL of ether was cooled to –60° C. and treated with TMEDA (7.1 mL, 46.9 mmol) followed by sec-BuLi (49.2 mL, 51.66 mmol) dropwise. The mixture was slowly warmed to –20° C. and stirred for 30 min and then cooled to –78° C. The mixture was treated with a solution of DMF (5.5 mL, 70.44 mmol) in 16 mL of ether via syringe, stirred for 10 min, and then quenched with 75 mL saturated ammonium chloride solution. The mixture was warmed to room temperature, and the organic layer was separated. The aqueous layer was extracted with ether, and the combined extracts were dried over $K_2CO_3$. The organic layer was concentrated to give a crude product as an oil which was chromatographed on silica with hexanes:EtOAc (4:1) to afford 6.5 g (66%) of the trans isomer and 2.1 g (21%) of the cis isomer. Both products were homogeneous by TLC analysis, with the cis isomer positiioned just above the trans isomer. $^1$H NMR (250 MHz) δ9.28–9.26 (d, 1 H), 4.25 (br. d, 1 H), 3.64–3.57 (m, 1H), 1.74–1.46 (m, 15 H), 1.09–1.04 (d, 3 H); $^{13}$C NMR (62.7 MHz) 196.3 (s), 155.1 (s), 77.4 (s), 59.2 (s), 47.3 (s), 29.3 (s), 28.2 (s), 25.4 (s), 16.3 (s) ppm.

N-Boc-2-(cis-1-Propenyl)Piperidine

A suspension of ethyltriphenylphosphonium bromide (7.31 g, 19.68 mmol) in 40 mL of THF was cooled to –30° C. and treated with n-BuLi (10.9 mL, 19.68 mmol) dropwise. The deep red solution was slowly warmed to 0° C., stirred for 30 min, and then cooled to –78° C. The ylide was treated with a solution of N-Boc-piperidine-2-carboxaldehyde (3.53 g, 17.89 mmol) in 10 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 1.6 g (41%) of the product which was homogenous by TLC analysis. $^1$H NMR (250 MHz) δ5.73–5.51 (m, 2 H), 5.05–5.01 (m, 1 H), 3.98–3.93 (br d, 1 H), 2.90–2.81 (m, 1 H), 1.7–1.39 (m, 18 H); $^{13}$C NMR (62.7 MHz) 154.8 (s), 128.0 (s), 125.8 (s), 79.0 (s), 47.7 (s), 39.6 (s), 30.3 (s), 28.5 (s), 25.6 (s), 19.5 (s), 13.2 (s) ppm.

N-Boc-2-propylpiperidine

A solution of the 1.5 g (6.66 mmol) of N-Boc-2-(cis-1-propenyl)piperdine in 2 mL of ethanol was shaken under 58 psi $H_2$ pressure over 0.3 g Pd/C catalyst overnight, and then the mixture was filtered through Celite and concentrated to give 1.43 g (94%) of the product as a clear colorless oil. No further purification was necessary. $^1$H NMR (250 MHz) δ4.21–4.17 (br s, 1 H), 3.98–3.92 (br d, I H), 2.79–2.68 (dt, 1 H), 1.67–1.23 (m, 19 H), 0.93–0.88 (t, 3 H); $^{13}$C NMR (62.7 MHz) 155.1 (s), 78.9 (s), 50.0 (s), 38.6 (s), 31.8 (s), 28.4 (s), 25.6 (s), 19.1 (s), 18.9 (s), 14.0 (s) ppm.

N-Boc-2-methyl-6-propylpiperidine

A solution of N-Boc-2-propylpiperidine (1.35 g, 5.94 mmol)was cooled to –60° C. and treated with TMEDA (1.2 mL, 7.66 mmol), followed by sec-BuLi (6.2 mL, 7.66 mmol) dropwise. The mixture was slowly warmed to –20° C., stirred for 30 min, and then cooled to –78° C. The mixture was treated with a solution of dimethyl sulfate (1.1 mL, 11.9 mmol) in ether and slowly warmed to room temperature. The mixture was diluted with water and then extracted with ether. The combined extracts were dried over $K_2CO_3$ and concentrated to give a crude product as an oil which was chromatographed on silica with 5% EtOAc/hexane to give 1.43 (95.8%) of the product which was homogeneous by TLC analysis. $^1$H NMR (250 MHz) δ3.94–3.88 (m, 1 H), 3.82–3.78 (m, 1 H), 1.87–1.21 (m, 21 H), 0.93–0.88 (t, 3 H); $^{13}$C NMR (62.7 MHz) 155.1 (s), 78.6 (s), 51.3 (s), 46.8 (s), 36.4 (s), 31.8 (s), 28.5 (s), 26.8 (s), 25.6 (s), 23.1 (s), 20.7 (s), 20.1 (s), 19.4 (s), 13.9 (s), 13.7 (s) ppm.

trans-2-methyl-6-n-propylpiperidine hydrochloride

To a stirred solution of the N-Boc-2-methyl-6-propylpiperidine (1.34 g, 5.6 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give teans-2-methyl-6-propylpiperdine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 124–125.9° C.; $^1$H NMR (300 MHz) δ9.92 (s, 2H), 3.54 (s, 1H), 3.29 (s, 1H), 2.0–1.2 (m, 13 H), 0.91 (t, 3H); $^{13}$C NMR (75 MHz) δ51.38 (s), 47.82 (s), 32.68 (s), 28.73 (s), 26.14 (s), 18.93 (s), 17.24 (s), 16.69 (s), 13.65 (s) ppm. FT-IR (neat): 3409, 2939, 1591, 1433, 1376, 1183, 1067, 993, 881. MS m/z 142, 141, 140, 126, 98, 84, 81, 70, 55, 44, 41. Elemental Analysis for $C_9H_{20}NCl$: C, 60.81%; H, 11.36%; N, 7.88%. Found: C, 60.72%; H, 11.30%; N, 7.82%.

N-Boc-2-(cis-1-Butenyl)Piperidine

A suspension of propyltriphenylphosphonium bromide (12.01 g, 31.2 mmol) in 60 mL of THF was cooled to –30° C. and treated with n-BuLi (12.5 mL, 31.2 mmol) dropwise. The deep red solution was slowly warmed to 0° C., stirred for 30 min, and then cooled to –78° C. The ylide was treated with a solution of N-Boc-piperidine-2-carboxaldehyde (4.1 g, 20.8 mmol) in 10 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 3.3 g (67%) of the product which was homogenous by TLC analysis. $^1$H NMR (250 MHz) δ5.68–5.39 (m, 2 H), 5.01–4.97 (m, 1 H), 3.92–3.88 (br d, 1 H), 2.87–2.78 (dt, 1 H), 2.13–2.06 (m, 2 H), 1.64–1.22 (m, 17 H), 0.96–0.91 (t, 3 H); $^{13}$C NMR (62.7 MHz) 154.6 (s), 133.4 (s), 126.3 (s), 47.8 (s), 39.5 (s), 31.5 (s), 30.6 (s), 28.4 (s), 28.2 (s), 25.5 (s), 22.5 (s), 20.8 (s), 19.4 (s), 14.1 (s) ppm.

N-Boc-2-ButylPiperidine

A solution of N-Boc-2-(1-butenyl)piperdine (3.1, 12.95 mmol) in 6 mL of ethanol was shaken under 58 psi of $H_2$ pressure over 0.62 g Pd/C catalyst overnight, and then the mixture was filtered through Celite and concentrated to give 2.94 (94%) of the product. No further purification was necessary. $^1$H NMR (250 MHz) δ4.18–4.16 (br s, 1 H), 3.96–3.92 (br d, 1 H), 2.78–2.69 (dt, 1 H), 1.69–1.17 (m, 21 H), 0.91–0.86 (t, 3 H).

N-Boc-2-Butyl-6-methylPiperidine

A solution of N-Boc-2-butylpiperidine (2.94 g, 12.18 mmol) in 40 mL of ether was cooled to −60° C. and treated with TMEDA (2.4 mL, 15.83 mmol), followed by sec-BuLi (13.0 mL, 15.83 mmol) dropwise. The mixture was slowly warmed to −20° C., stirred for 30 min, and then cooled to −78° C. The mixture was treated with solution of dimethyl sulfate (2.3 mL, 24.36 mmol) in ether and slowly warmed to room temperature. The mixture was diluted with water and then extracted with ether. The combined extracts were dried over $K_2CO_3$ and concentrated to give a crude product as an oil which was chromatographed on silica with 5% EtOAc/hexane to give 3.11 (87%) of the product which was homogeneous by TLC analysis. No cis isomer was detected. $^1$H NMR (250 MHz) δ3.92–3.81 (m, 1 H), 3.80–3.79 (m, 1 H), 1.66–1.21 (m, 24 H), 0.91–0.86 (t, 3 H).

trans-2-butyl-6-methylpiperidine hydrochloride

To a stirred solution of the N-Boc-2-butyl-6-methylpiperidine (2.7 g, 10.57 mmol) in 15% trifloroacetic acid (70 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give teans-2-methyl-6-butylpiperdine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give 1.43 g (71%) of the piperidinium hydrochloride as a white solid. mp 118.0–119.0° C.; $^1$H NMR (250 MHz) δ9.87 (s, 2H), 3.53 (s, 1H), 3.27 (s, 1H), 2.0–1.2 (m, 15H), 0.90 (t, 3H); $^{13}$C NMR (62.7 MHz) δ51.57 (s), 47.78 (s), 30.22 (s), 28.78 (s), 26.05 (s), 22.28 (s), 17.24 (s), 16.78 (s), 13.81 (s) ppm. FT-IR (neat): 3430, 2954, 2925, 1584, 1558, 1456, 1418, 1339, 1028, 1009. MS m/z 156, 155, 154, 140, 98, 84, 81, 70, 55, 44, 41. Elemental Analysis for $C_{10}H_{22}NCl$: C, 62.63%; H, 11.59%; N, 7.30%. Found: C, 62.67%; H, 11.52%; N, 7.34%.

N-Boe-2-(cis-1-Heptenyl)Piperidine

A suspension of heptyltriphenylphosphonium bromide (13.0 g, 3 0.41 mmol) in 60 mL of THF was cooled to -300 C and treated with n-BuLi (12.2 mL, 30.41 mmol) dropwise. The deep red solution was slowly warmed to 0° C., stirred for 30 min, and then cooled to −78° C. The ylide was treated with a solution of N-Boc-piperidine-2-carboxaldehyde (4.0 g, 20.27 mmol) in 7 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 5.7 g (70%) of the product that was homogeneous by TLC analysis. $^1$H NMR (250 MHz) δ5.72–5.49 (pair of m, 2 H), 5.02–4.96 (br s, 1 H), 3.97–3.89 (br d, 1 H), 2.89–2.76 (dt, 1 H), 2.14–1.99 (m, 2 H), 1.61–1.24 (m, 21 H), 0.88–0.83 (t, 3 H); $^{13}$C NMR (62.7 MHz) 154.6 (s), 133.3 (s), 127.8 (s), 78.9 (s), 48.8 (s), 39.5 (s), 32.3 (s), 30.9 (s), 30.6 (s), 27.6 (s), 25.9 (s), 23.9 (s), 22.5 (s), 21.1 (s), 19.4 (s), 16.9 (s), 14.8 (s), 13.2 (s) ppm.

N-Boc-2-HeptylPiperidine

A solution of N-Boc-2-(1-heptenyl)piperdine (3.92, 13.93 mmol) in 7 mL of ethanol was shaken under 58 psi of $H_2$ pressure over 0.78 g Pd/C catalyst overnight, and then the mixture was filtered through Celite and concentrated to give 3.94 g (quantitative) of the product. No further purification was necessary. $^1$H NMR (250 MHz) δ4.20–4.15 (br s, 1 H), 3.99–3.85 (br d, 1 H), 2.79–2.70 (dt, 1 H), 1.59–1.25 (m, 21 H), 0.89–0.85 (t, 3 H); $^{13}$C NMR (62.7 MHz) 155.1 (s), 78.8 (s), 50.3 (s), 38.6 (s), 31.8 (s), 29.6 (s), 29.5 (s), 29.3 (s), 28.4 (s), 26.3 (s), 25.6 (s), 22.6 (s), 18.9 (s), 14.0 (s) ppm.

N-Boc-2-Heptyl-6-methylPiperidine

A solution of N-Boc-2-heptylpiperidine (4.00 g, 14.11 mmol) in 40 mL of ether was cooled to −60° C. and treated with TMEDA (2.8 mL, 18.34 mmol), followed by sec-BuLi (14.1 mL, 18.34 mmol) dropwise. The mixture was slowly warmed to −20° C., stirred for 30 min, and then cooled to −78° C. The mixture was treated with a solution of dimethyl sulfate (3.6 mL, 28.22 mmol) in 13 mL of ether and slowly warmed to room temperature. The mixture was diluted with water and then extracted with ether. The combined extracts were dried over $K_2CO_3$ and concentrated to give a crude product as an oil which was chromatographed on silica with 5% EtOAc/hexane to give 3.11 (87%) of the product which was homogeneous by TLC analysis. No cis isomer was detected. $^1$H NMR (250 MHz) δ3.94–3.81 (m, 1 H), 3.82–3.80 (m, 1 H), 1.70–1.23 (m, 30 H), 0.91–0.86 (t, 3 H).

trans-2-heptyl-6-methylpiperidine hydrochloride

To a stirred solution of the N-Boc-2-heptyl-6-methylpiperidine (2.7 g, 10.57 mmol) in 15% trifloroacetic acid (70 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give teans-2-methyl-6-heptylpiperdine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 123–125° C.; $^1$H NMR (250 MHz) δ9.29 (s, 2H), 3.51 (s, 1H), 3.25 (s, 1H), 2.0–1.2 (m, 21H), 0.85 (t, 3H); $^{13}$C NMR (62.7 MHz) 51.7 (s), 47.9 (s), 31.7 (s), 30.7 (s), 29.2 (s), 2.91 (s), 28.8 (s), 26.1 (s), 25.8 (s), 22.5 (s), 17.3 (s), 16.8 (s), 14.0 (s) ppm. FT-IR (neat): 3420, 2956, 2919, 1587, 1470, 1463, 1454, 1393, 1360, 1184, 1125, 890. Elemental Analysis for $C_{13}H_{28}NCl$: C, 66.76%; H, 12.09%; N, 5.99%. Found: C, 66.58%; H, 12.06%; N, 6.01%.

trans-N-Boc-2-methyl-6-(2-phenylethenyl)piperidine

A suspension of benzyltriphenylphosphonium bromide (10.3 g, 26.5 mmol) in 54 mL of THF was cooled to −30° C. and treated with n-BuLi (11.2 mL, 26.88 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (4.00 g, 18.93 mmol) in 6 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded3.8 g (66%) of the product which was homogeneous by TLC analysis. $^1$H NMR (250 MHz) δ7.35–7.19 (m, 5 H), 6.38–6.34 (m, 1 H), 5.80–5.76 (m, 1 H), 4.74–4.67, (m, 1 H), 4.35–4.18 (m, 1 H), 1.80–0.88 (m, 18 H).

trans-N-Boc-2-methyl-6-(2-phenylethyl)piperidine

A solution of trans-N-Boc-2-methyl-6-(2-phenylethenyl) piperidine (3.8, 12.54 mmol) in 6 mL of ethanol was shaken under 58 psi of $H_2$ pressure over 0.70 g Pd/C catalyst overnight, and then the mixture was filtered through Celite and concentrated to give 3.81 g (quantitative) of the product. No further purification was necessary. $^1$H NMR (250 MHz) δ7.30–7.14 (m, 5 H), 3.93–3.89 (m, 2 H), 2.64–2.59 (t, 2 H), 1.98–1.20 (m, 20 H).

trans-2-methyl-6-(2-phenylethyl)piperidine hydrochloride

To a stirred solution of trans-N-Boc-2-methyl-6-(2-phenylethyl)piperidine (1.4 g, 5.50 mmol) in 15% trifloroacetic acid (35 mL) in dichloromethane was stirred for 2 h at room temperature, and the reaction mixture was quenched with 65 mL saturated $NaHCO_3$ solution. The mixture was extracted with ether *5 and the combined extracts were dried over $K_2CO_3$ and then concentrated to give trans-2-methyl-6-(2-phenylethyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 148.3–151.0; $^1$HNMR (300 MHz) δ9.3, (s, 2H), 7.28–7.11 (m, 5H), 3.43 (s, 1H), 3.19 (s, 1H), 2.67–1.27 (m, 13H); $^{13}$C NMR (75 MHz) 140.0 (s), 128.3 (s), 126.1 (s), 50.9 (s), 47.9 (s), 32.1 (s), 31.5 (s), 28.5 (s), 26.4 (s), 17.2 (s), 16.5 (s). FT-IR (neat): 3410, 3075, 2944, 1590, 1494, 1454, 1435, 1336, 1122, 1029, 751, 701. Elemental Analysis for $C_{14}H_{22}NCl$: C, 70.11%; H, 9.27%; N, 5.84%. Found: C, 69.95%; H, 9.19%; N, 5.79%.

N-Boc-2-(cis-1-Ethenyl)Piperidine

A suspension of methyltriphenylphosphonium bromide (10.86 g, 30.41 mmol) in 60 mL of THF was cooled to −30° C. and treated with n-BuLi (13.5 mL, 30.41 mmol) dropwise. The deep red solution was slowly warmed to 0° C., stirred for 30 min, and then cooled to −78° C. The ylide was treated with a solution of N-Boc-piperidine-2-carboxaldehyde (4.0 g, 20.27 mmol) in 10 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 2.3 g (55%) of the product which was homogeneous by TLC analysis. $^1$H NMR (250 MHz) δ5.78–5.67 (m, 1 H), 5.16–4.97 (m, 2 H), 4.87–4.82 (br s, 1 H), 3.95–3.88 (br d, 1 H), 2.85–2.74 (dt, 1 H), 1.87–1.37 (m, 15 H); ); $^{13}$C NMR (62.7 MHz) 155.3 (s), 136.8 (s), 115.4 (s), 79.2 (s), 52.4 (s), 39.6 (s), 28.5 (s), 28.3 (s), 25.5 (s), 19.4 (s) ppm.

N-Boc-2-ethylpiperidine

A solution of the (2.25 g, 10.65 mmol) of N-Boc-2-(cis-1-ethenyl)piperdine in 3 mL of ethanol was shaken under 58 psi $H_2$ pressure over 0.3 g Pd/C catalyst overnight, and then the mixture was filtered through Celite and concentrated to give 1.78 g (82%) of the product as a clear colorless oil. No further purification was necessary. $^1$H NMR (250 MHz) δ4.11–4.05 (br s, 1 H), 3.97–3.93 (br d, 1 H), 2.75–2.66 (dt, 1 H), 1.84–1.33 (m, 17 H), 0.85–0.80 (t, 3 H); $^{13}$C NMR (62.7 MHz) 154.7 (s), 78.8 (s), 51.8 (s), 38.6 (s), 28.4 (s), 28.0 (s), 25.6 (s), 22.5 (s), 18.9 (s), 10.8 (s)ppm.

N-Boc-2-Ethyl-6-methylPiperidine

A solution of N-Boc-2-ethylpiperidine (1.5 g, 7.0 mmol) in 28 mL of ether was cooled to −60° C. and treated with TMEDA (1.6 mL, 10.85 mmol), followed by sec-BuLi (8.5 mL, 10.85 mmol) dropwise. The mixture was slowly warmed to −20° C., stirred for 30 min, and then cooled to −78° C. The mixture was treated with a solution of dimethyl sulfate (1.6 mL, 16.69 mmol) in ether and slowly warmed to room temperature. The mixture was diluted with water and then extracted with ether. The combined extracts were dried over $K_2CO_3$ and concentrated to give a crude product as an oil which was chromatographed on silica with 5% EtOAc/hexane to give 0.88 g (59%) of the product which was homogeneous by TLC analysis. $^1$H NMR (250 MHz) δ3.91–3.87 (m, 1 H), 3.69–3.65 (m, 1 H), 1.83–1.41 (m, 17 H), 1.21–1.19 (d, 3 H), 0.85–0.82 (t, 3 H); $^{13}$C NMR (62.7 MHz) 155.2 (s), 78.6 (s), 53.0 (s), 46.8 (s), 28.5 (s), 27.2 (s), 26.7 (s), 22.4 (s), 20.7 (s), 13.4 (s), 11.4 (s) ppm.

trans-2-ethyl-6-methylpiperidine hydrochloride

To a stirred solution of the N-Boc-2-ethyl-6-methylpiperidine (0.88 g, 3.87 mmol) in 15% trifloroacetic acid (15 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give teans-2-ethyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 174.9–175.2° C.; $^1$H NMR (250 MHz) δ9.33 (s, 2H), 3.54 (s, 1H), 3.19 (s, 1H), 2.07–1.46 (m, 13H), 0.99 (t, 3H); $^{13}$C NMR (62.7 MHz) 53.0 (s), 47.9 (s), 28.8 (s), 25.6 (s), 2.38 (s), 17.2 (s), 16.8 (s), 10.2 (s) ppm. FT-IR (neat): 3420, 2931, 1588, 1455, 1393, 1186, 1065, 960. Elemental Analysis for $C_8H_{18}NCl$: C, 58.69%; H, 11.11%; N, 8.55%. Found: C, 58.64%; H, 11.09%; N, 8.56%.

trans-N-Boc-2-methyl-6-(1-propenyl)piperidine

A suspension of ethyltriphenylphosphonium bromide (4.92 g, 13.25 mmol) in 27 mL of THF was cooled to −30° C. and treated with n-BuLi (5.41 mL, 13.25 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (2.00 g, 9.46 mmol) in 3 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 2.26 g (81%) of the product which was homogeneous by TLC analysis. $^1$H NMR (250 MHz) δ(5.51–5.38 (m, 2 H), 4.61–4.56 (m, 1 H), 4.08 (m, 1 H), 1.91–1.19 (m, 21 H); $^{13}$C NMR (62.7 MHz) 155.2 (s), 133.5 (s), 122.9 (s), 78.9 (s), 48.8 (s), 47.3 (s), 28.5 (s), 28.3 (s), 27.7 (s), 20.3 (s), 14.7 (s), 12.8 (s) ppm.

trans-2-methyl-6-(1-propenyl)piperidine hydrochloride

To a stirred solution of trans-N-Boc-2-methyl-6-(1-propenyl)piperidine (1.80 g, 7.65 mmol) in 15% trifloroacetic acid (38 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-methyl-6-(1-propenyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid that was homogeneous by TLC analysis. mp 139.5–141.1° C.; $^1$H NMR (250 MHz) δ9.39 (s, 2H), 5.84–5.86 (m, 2H), 4.23 (s, 1H), 3.54 (s, 1H), 1.9–1.44 (m, 12H); $^{13}$C NMR (62.7 MHz) 131 (s), 123 (s), 48 (s), 28.5 (s), 28 (s), 17.6 (s), 17.1 (s), 13.7 (s) ppm. FT-IR (neat ): 3420, 3020, 2944, 1588, 1459, 1434, 1386, 821, 816, 804. Elemental Analysis for $C_9H_{18}NCl$: C, 61.52%; H, 10.35%; N, 7.97%. Found: C, 61.44%; H, 10.29%; N, 7.88%.

trans-N-Boc-2-(1-butenyl)-6-methylpiperidine

A suspension of propyltriphenylphosphonium bromide (5.11 g, 13.25 mmol) in 27 mL of THF was cooled to −30° C. and treated with n-BuLi (6.31 mL, 13.25 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (2.00 g, 9.46 mmol) in 3 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 1.80 g (80%) of the product a clear oil which was homogeneous by TLC analysis. $^1$H NMR (250 MHz) δ5.48–5.31 (m, 2 H), 4.59–4.54 (m, 1 H), 4.07–4.00 (m, 1 H), 2.12–1.38 (m, 15 H), 1.23–1.19 (d, 3 H), 0.97–0.95 (t, 3 H); $^{13}$C NMR (62.7 MHz) 155.5 (s), 131.9 (s), 130.8 (s), 78.9 (s), 49.0 (s), 47.4 (s), 28.5 (s), 28.2 (s), 27.8 (s), 20.6 (s), 20.2 (s), 14.9 (s), 1.42 (s)ppm.

trans-2-(1-butenyl)-6-methylpiperidine hydrochloride

To a stirred solution of trans-N-Boc-2-(1-butenyl)-6-methylpiperidine (1.80 g, 7.65 mmol) in 15% trifloroacetic acid (38 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-(1-butenyl)-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid that was homogeneous by TLC analysis. mp 167–169.0° C.; $^1$H NMR (250 MHz) δ9.4 (s, 2H), 5.71–5.58 (m, 2H), 4.17 (s, 1H), 3.54 (s, 1H), 2.2–1.4 (m, 11H), 0.98(t, 3H); $^{13}$C NMR (62.7 MHz) δ138.5 (s), 122.4 (s), 48.2 (s), 47.9 (s), 28.74 (s), 28.45 (s), 21.3 (s), 17.6 (s), 16.9 (s), 13.8 (s). FT-IR (neat): 3425, 3183, 3072, 2961, 2915, 1656, 1585, 1463, 1443, 1407, 1107, 1075, 960, 883, 803. Elemental Analysis for $C_{10}H_{20}NCl$: C, 63.29%; H, 10.65%; N, 7.38%. Found: C, 63.14%; H, 10.58%; N, 7.32%.

trans-N-Boc-2-(1-pentenyl)-6-methylpiperidine

A suspension of methyltriphenylphosphonium bromide (5.29 g, 13.25 mmol) in 27 mL of THF was cooled to −30° C. and treated with n-BuLi (6.13 mL, 13.44 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (2.00 g, 9.46 mmol) in 3 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 2.53 g (87%) of the product which was homogeneous by TLC analysis. $^1$H NMR (250 MHz) δ5.48–5.28 (m, 2 H), 4.58–4.54 (m, 1 H), 4.06–4.03 (m, 1 H), 2.10–1.23 (m, 19 H), 1.22–1.18 (d, 3 H), 0.93–0.88 (t, 3 H), 1 H), 4.07–4.00 (m, 1 H), 2.12–1.38 (m, 15 H), 1.23–1.19 (d, 3 H), 0.97–0.95 (t, 3 H); $^{13}$C NMR (62.7 MHz) 155.5 (s), 132.4 (s), 129.2 (s), 78.9 (s), 49.1 (s), 47.5 (s), 29.4 (s), 28.5 (s), 28.2 (s), 27.8 (s), 22.8 (s), 20.2 (s), 15.0 (s), 13.9 (s) ppm.

trans-2-(1-pentenyl)-6-methylpiperidine hydrochloride

To a stirred solution of trans-N-Boc-2-(1-pentenyl)-6-methylpiperidine (2.5 g, 9.35 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give trans-2-(1-pentenyl)-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid that was homogeneous by TLC analysis. mp 150.4–150.9° C.; $^1$H NMR (250 MHz) δ9.5–9.3 (br. d, 2H), 5.74–5.62 (m, 2H), 4.19 (s, 1H), 3.55 (s, 1H), 2.1–1.3 (m, 13H), 0.87 (t, 3H); $^{13}$C NMR (62.7 MHz) δ136.8 (s), 123.0 (s), 48.3 (s), 47.9 (s), 29.9 (s), 28.8 (s), 28.4 (s), 22.3 (s), 17.6 (s), 17.1 (s), 13.8 (s). FT-IR (neat): 3424, 3171, 2939, 1635, 1597, 1582, 1459, 1432, 1384, 1287, 1123, 1075, 895. Elemental Analysis for $C_{11}H_{22}NCl$: C, 64.83%; H, 10.9%; N, 6.87%. Found: C, 64.77%; H, 10.82%; N, 6.85%.

trans-N-Boc-2-methyl-6-(1-isopentenyl)piperidine

A suspension of isobutyltriphenylphosphonium bromide (10.58 g, 26.5 mmol) in 42 mL of THF was cooled to −30° C. and treated with n-BuLi (12.2 mL, 26.88 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (4.00 g, 18.93 mmol) in 6 mL of THF, and the mixture was slowly warmed to room temperature. The mixture was diluted with water, and the organic layer was separated. The aqueous layer was extracted with ether and the combined extracts were dried over $K_2CO_3$ and then concentrated to give a crude product as an oil. Chromatography on silica with 5% EtOAc/hexane afforded 3.2 g (63%) of the product which was homogeneous by TLC analysis. $^1$H NMR (250 MHz) δ5.41–5.14 (m, 2 H), 4.62–4.58 (m, 1 H), 4.05–4.01 (m, 1 H), 2.69–2.68 (m, 1 H), 1.90–1.38 (m, 15 H), 1.23–1.20 (d, 3 H), 0.93–0.87 (t, 6 H); $^{13}$C NMR (62.7 MHz) 156.1 (s), 136.8 (s), 129.8 (s), 79.0 (s), 49.1 (s), 47.5 (s), 28.7 (s), 28.5 (s), 27.9 (s), 26.6 (s), 23.3 (s), 23.0 (s), 20.2 (s), 15.1 (s) ppm.

trans-N-Boc-2-methyl-6-isopentylpiperidine

A solution of trans-N-Boc-2-methyl-6-(1-isopentenyl) piperidine (1.5, 5.61 mmol) in 3 mL of ethanol was shaken under 58 psi of $H_2$ pressure over 0.31 g Pd/C catalyst overnight, and then the mixture was filtered through Celite and concentrated to give 1.51 (99%) of the product. No further purification was necessary. ¹H NMR (250 MHz) δ3.94–3.87 (m, 1 H), 3.81–3.72 (m, 1 H), 1.89–1.15 (m, 23 H), 0.88–0.85 (d, 6 H); ¹³C NMR (62.7 MHz) 155.2 (s), 78.6 (s), 51.9 (s), 46.8 (s), 36.3 (s), 3.21 (s), 28.5 (s), 28.0 (s), 26.9 (s), 23.1 (s), 22.7 (s), 22.5 (s), 20.8 (s), 13.6 (s) ppm.

trans-2-methyl-6-isopentylpiperidine hydrochloride

To a stirred solution of trans-N-Boc-2-methyl-6-isopentylpiperidine (1.5 g, 5.56 mmol) in 15% trifluoroacetic acid (35 mL) in dichloromethane was stirred for 2 h at room temperature, and the reaction mixture was quenched with 90 mL saturated NaHCO₃ solution. The mixture was extracted with ether *5 and the combined extracts were dried over K₂CO₃ and then concentrated to give trans-2-methyl-6-isopentylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 134.1–134.7° C.; ¹H NMR (250 MHz) 67 9.36 (s, 2H), 3.53 (s, 1H), 3.25 (s, 1H), 1.96–1.1 (m, 14H), 0.88–0.82 (d, 6H); ¹³C NMR (62.7 MHz) δ51.9 (s), 47.8 (s), 34.7 (s), 28.9 (s), 28.4 (s), 27.8 (s), 26.0 (s), 22.7 (s), 22.1 (s), 17.3 (s), 16.9 (s). FT-IR (neat): 3422, 2949, 1636, 1602, 1587, 1500, 1422, 1384, 1230, 1105, 1030, 998, 895. Elemental Analysis for $C_{11}H_{24}NCl$: C, 64.20%; H, 11.78%; N, 6.80%. Found: C, 64.08%; H, 11.72%; N, 6.78%.

trans-2-methyl-6-(1-isopentenyl)piperidine hydrochloride

To a stirred solution of trans-N-Boc-2-methyl-6-(1-isopentenyl)piperidine (1.5 g, 5.56 mmol) in 15% trifluoroacetic acid (35 mL) in dichloromethane was stirred for 2 h at room temperature, and the reaction mixture was quenched with 90 mL saturated NaHCO₃ solution. The mixture was extracted with ether *5 and the combined extracts were dried over K₂CO₃ and then concentrated to give trans-2-methyl-6-(1-isopentenyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 157.5–156.5° C.; ¹H NMR (250 MHz) δ9.37 (br. d, 2H), 5.59–5.46 (m, 2H), 4.19 (s, 1H), 3.59 (s, 1H), 2.66–2.59 (m, 1H), 1.8–1.5 (m, 9H), 1.0 (pair of d, 6H); ¹³C NMR (62.7 MHz) δ143.6 (s), 120.6 (s), 48.3 (s), 47.9 (s), 28.9 (s), 28.6 (s), 27.3 (s), 23.01 (s), 22.6 (s), 17.5 (s), 16.9 (s). FT-IR (neat): 3426, 3188, 3018, 2952, 1625, 1584, 1464, 1359, 1180, 1099, 958, 881. Elemental Analysis for $C_{11}H_{22}NCl$: C, 64.84%; H, 10.91%; N, 6.87%. Found: C, 64.06%; H, 10.77%; N, 6.78%.

trans-N-Boc-2-(1-isohexenyl)-6-methylpiperidine

A suspension of isoamyltriphenylphosphonium bromide (10.95 g, 26.5 mmol) in 42 mL of THF was cooled to −30° C. and treated with n-BuLi (11.9 mL, 26.88 mmol) dropwise. The deep red solution was slowly warmed to 0° C., stirred for 30 min, and then cooled to −78° C. The ylide was treated with a solution of trans-N-Boc-2-Methyl-6-Piperidinecarboxaldehyde (4.00 g, 18.93 mmol) in 6 mL of THF, and the mixture was slowly warmed to room temperature. The mixture was diluted with water, and the organic layer was separated. The aqueous layer was extracted with ether and the combined extracts were dried over K₂CO₃ and then concentrated to give a crude product as an oil. Chromatography on silica with 5% EtOAc/hexane afforded 2.8 g (56%) of the product which was homogeneous by TLC analysis. ¹H NMR (250 MHz) δ5.53–5.32 (m, 2 H), 4.56–4.51 (m, 1 H), 4.04–4.02 (m, 1 H), 1.99–1.37 (m, 18 H), 1.23–1.18 (d, 3H), 0.91–0.84 (d, 6 H); ¹³C NMR (62.7 MHz) 155.5 (s), 132.8 (s), 128.2 (s), 78.9 (s), 49.1 (s), 47.6 (s), 36.4 (s), 28.6 (s), 28.5 (s), 28.0 (s), 27.9 (s), 26.3 (s), 25.6 (s), 22.5 (s), 22.4 (s), 20.7 (s), 20.2 (s), 15.2 (s), 13.6 (s) ppm.

trans-N-Boc-2-isohexyl-6-methylpiperidine

A solution of trans-N-Boc-2-(1-isohexenyl)-6-methylpiperidine (1.35, 4.79 mmol) in 4 mL of ethanol was shaken under 58 psi of H₂ pressure over 0.34 g Pd/C catalyst overnight, and then the mixture was filtered through Celite and concentrated to give 1.40 g (quantitative) of the product. No further purification was necessary. ¹H NMR (250 MHz) δ3.92–3.90 (m, 1 H), 3.79–3.76 (m, 1 H), 1.84–1.14 (m, 28 H), 0.87–0.82 (d, 6 H); ¹³C NMR (62.7 MHz) 154.7, 78.6, 51.6, 46.9, 38.9, 34.5, 28.5, 27.9, 26.8, 24.8, 23.2, 22.6, 22.5, 20.8, 13.7 ppm.

trans-2-isohexyl-6-methylpiperidine hydrochloride

To a stirred solution of trans-N-Boc-2-isohexyl-6-methylpiperidine (1.4 g, 5.50 mmol) in 15% trifloroacetic acid (35 mL) in dichloromethane was stirred for 2 h at room temperature, and the reaction mixture was quenched with 90 mL saturated NaHCO₃ solution. The mixture was extracted with ether *5 and the combined extracts were dried over K₂CO₃ and then concentrated to give trans-2-isohexyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 155.0–156.0° C.; ¹H NMR (250 MHz) δ9.17 (s, 2H), 3.50 (s, 1H), 3.25 (s, 1H), 1.94–1.15 (m, 16H), 0.82 (d, 6H); ¹³C NMR (62.7 MHz) δ51.7 (s), 47.9 (s), 38.4 (s), 30.9 (s), 28.8 (s), 27.8 (s), 26.1 (s), 23.5 (s), 22.5 (s), 22.3 (s), 17.3 (s), 16.8 (s) ppm. FT-IR (neat): 3430, 2948, 1615, 1589, 1557, 1472, 1436, 1418, 1362, 1102, 895. Elemental Analysis for $C_{12}H_{26}NCl$: C, 65.56%; H, 11.95%; N, 6.37%. Found: C, 64.90%; H, 11.89%; N, 6.26%.

trans-2-isohexenyl-6-methylpiperidine hydrochloride

To a stirred solution of trans-N-Boc-2-isohexyl-6-methylpiperidine (1.4 g, 5.50 mmol) in 15% trifloroacetic acid (35 mL) in dichloromethane was stirred for 2 h at room temperature, and the reaction mixture was quenched with 70 mL saturated NaHCO₃ solution. The mixture was extracted with ether *5 and the combined extracts were dried over K₂CO₃ and then concentrated to give trans-2-isohexenyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 164.2–167.0° C.; ¹H NMR (250 MHz) δ9.44 (s, 2H), 5.71 (s, 2H), 4.18 (s, 1H), 3.56 (s, 1H), 2.0–1.5 (m, 12H), 0.94 (dd, 6H); ¹³C NMR (62.7 MHz) δ135.7 (s), 123.6 (s), 4.84 (s), 47.9 (s), 36.9 (s), 28.9 (s), 28.4 (s), 28.2 (s), 22.5 (s), 22.1 (s), 17.6 (s), 17.2 (s) ppm. FT-IR (neat): 3429, 3165, 2940, 1620, 1550, 1478, 1400, 1354, 1097, 890. Elemental Analysis for $C_{12}H_{24}NCl$: C, 66.17%; H, 11.13%; N, 6.43%. Found: C, 66.25%; H, 11.05%; N, 6.50%.

trans-2-heptenyl-6-methylpiperidine hydrochloride

To a stirred solution of the N-Boc-2-heptenyl-6-methylpiperidine (1.5g, 5.08 mmol) in 15% trifloroacetic acid (35 mL) in dichloromethane was stirred for 2 h at room temperature, and the reaction mixture was quenched with 90 mL saturated $NaHCO_3$ solution. The mixture was extracted with ether *5 and the combined extracts were dried over $K_2CO_3$ and then concentrated to give teans-2-heptenyl-6-methylpiperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 121.1–122.0° C.; $^1$H NMR($CDCl_3$) δ9.44 (s, 2H), 5.68 (m, 2H), 4.19 (s, 1H), 3.56 (s, 1H), 2.2–1.2 (m, 17H), 0.88 (t, 3H); $^{13}$C NMR ($CDCl_3$) δ137.1 (s), 122.8 (s), 48.34 (s, 1H), 31.4 (s), 28.8 (s), 28.4 (s), 27.9 (s), 22.4 (s), 17.6 (s), 17.1 (s), 13.97 (s). FT-IR (near): 3435, 3192, 2924, 1586, 1431, 1030, 673. Elemental Analysis for $C_{13}H_{26}NCl$: C, 67.34%; H, 11.33%; N, 6.04%. Found: C, 67.44%; H, 11.23%; N, 5.98%.

trans-N-Boc-2-methyl-6-(ethenyl propionyl)piperidine

To a stirred solution of the trans-N-Boc-2-Methyl-6-Piperidinecarboxaldehyde in $CH_2Cl_2$ (25 mL), was added ylide (carbethoxymethylene)-triphenylphosphorane (8.24 g, 23.66 mmol). The mixture was stirred at reflux for 2 hours, and another half equivalent of the ylide was added (2 g) in 4 ml $CH_2Cl_2$. The mixture was stirred overnight, and was then refluxed for 2 hours more. The mixture was concentrated by evaporation. A small amount of $CH_2Cl_2$ was added, and the mixture was immediately purified with column chromatography (silica gel, 5% EtOAc in hexanes) to afford 2.01 g (80%) of the product that was homogeneous by TLC analysis. $^1$H NMR (250 MHz) δ7.02–6.95 (dd, 1H), 5.83–5.77 (d, 1 H), 4.46–4.42 (m, 1 H), 4.21–4.09 (m, 3 H), 2.03–1.10 (m, 21 H); $^{13}$C NMR (62.7 MHz) 166.6 (s), 155.2 (s), 151.1 (s), 119.2 (s), 79.6 (s), 60.1 (s), 59.1 (s), 51.9 (s), 47.2 (s), 29.2 (s), 28.3 (s), 26.7 (s), 26.3 (s), 19.7 (s), 16.2 (s), 14.2 (s) ppm.

trans-N-Boc-2-methyl-6-(ethyl propionyl)piperidine

A solution of trans-N-Boc-2-methyl-6-(ethenyl propionyl)piperidine (2.0 g, 6.70 mmol) in 3 mL of ethanol was shaken under 58 psi of $H_2$ pressure over 0.65 g Pd/C catalyst overnight, and then the mixture was filtered through Celite and concentrated to give 1.8 g (90%) of the product which was homogeneous by TLC analysis. $^1$H NMR (250 MHz) δ4.16–4.08 (q, 2 H), 3.93–3.83 (m, 2 H), 2.36–2.28 (t, 2 H), 2.04–1.08 (m, 20 H); $^{13}$C NMR (62.7 MHz) 155.4 (s), 79.1 (s), 60.3 (s), 51.0 (s), 47.2 (s), 31.9 (s), 29.6 (s), 28.5 (s), 26.9 (s), 25.8 (s), 24.2 (s), 20.5 (s), 14.2 (s), ppm.

trans-2-methyl-6-(ethyl propionyl)piperidine hydrochloride

To a stirred solution of trans-N-Boc-2-methyl-6-(ethyl propionyl)piperidine. (1.8 g, 6.01 mmol) in 15% trifloroacetic acid (35 mL) in dichloromethane was stirred for 2 h at room temperature, and the reaction mixture was quenched with 75 mL saturated $NaHCO_3$ solution. The mixture was extracted with ether *5 and the combined extracts were dried over $K_2CO_3$ and then concentrated to give trans-2-methyl-6-(ethyl propionyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 121.1–122.0° C.; $^1$H NMR (300 MHz) δ9.44 (s, 2H), 5.68 (m, 2H), 4.19 (s, 1H), 3.56 (s, 1H), 2.2–1.2 (m, 17H), 0.88 (t, 3H); $^{13}$C NMR (75 MHz) δ137.1 (s), 122.8 (s), 48.34 (s), 47.94 (s), 31.4 (s), 28.8 (s), 28.4 (s), 27.9 (s), 22.4 (s), 17.6 (s), 17.1 (s), 13.97 (s) ppm. FT-IR (neat): 3435, 3192, 2924, 1586, 1431, 1030, 673. Elemental Analysis. for $C_{13}H_{26}NCl$: C, 67.34%; H, 11.33%; N, 6.04%. Found: C, 67.44%; H, 11.23%; N, 5.98%.

trans-2-methyl-6-(ethenyl propionyl)piperidine hydrochloride

To a stirred solution of trans-N-Boc-2-methyl-6-(ethenyl propionyl)piperidine. (1.8 g, 3.36 mmol) in 15% trifloroacetic acid (35 mL) in dichloromethane was stirred for 2 h at room temperature, and the reaction mixture was quenched with 75 mL saturated $NaHCO_3$ solution. The mixture was extracted with ether *5 and the combined extracts were dried over $K_2CO_3$ and then concentrated to give trans-2-methyl-6-(ethenyl propionyl)piperidine as an oil. The crude oil was immediately dissolved in a small amount of ether, and ether saturated with HCl (g) was added slowly via pipette. This solution was allowed to stand for 10 minutes, and the solvent was evaporated. More ether was added and the flask was swirled constantly until crystallization occured. The solid was collected via filtration, and dried in vacuo to give the piperidinium hydrochloride as a white solid. mp 154.8–156.3; $^1$H NMR (300 MHz) δ9.89 (s, 2H), 7.03 (dd, 1H), 6.24 (d, 1H), 4.24–4.11 (m, 3H), 3.45 (s, 1H), 2.2–1.49 (m, 9H), 1.26–1.22 (t, 3H); $^{13}$C NMR (75 MHz) δ165.1 (s), 140.1 (s), 126.3 (s), 60.83 (s), 54.3 (s), 51.8 (s), 48.6 (s), 29.4 (s), 27.9 (s), 26.3 (s), 17.9 (s), 14.1 (s) ppm. FT-IR (neat): 3374, 3107, 2943, 1717, 1683, 1635, 1539, 1436, 1312, 1190, 1033, 981. Elemental Analysis for $C_{11}H_{20}NO_2Cl$: C, 56.52%; H, 8.64%; N, 5.99%. Found: C, 56.37%; H, 8.58%; N, 5.89%.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A method for reducing or eradicating a population or for reducing or preventing the spread of a colony of fire ants comprising exposing to said population of fire ants a composition comprising an effective amount of a trans-2,6-disubstituted piperidine compound according to the structure:

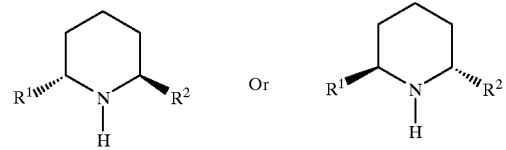

wherein $R^1$ and $R^2$ are selected from a $C_1$ to $C_{20}$ saturated or unsaturated linear, cyclic or branch-chained substituted or unsubstituted hydrocarbon group, a substituted or unsubstituted aromatic group or an ester group and salts thereof; in combination with a bait and optionally, a carrier.

2. The method according to claim 1 wherein said hydrocarbon group is an alkyl group.

3. The method according to claim 1 wherein said hydrocarbon group is an alkenyl group.

4. The method according to claim 2 wherein said alky group is a $C_2$ to $C_9$ alkyl group.

5. The method according to claim 1 wherein said hydrocarbon is a substituted or unsubstituted aromatic group.

6. The method according to claim 1 wherein said hydrocarbon is an aromatic substituted alkyl group.

7. The method according to claim 1 wherein said ester group contains a chemical structure according to the formula:

$$R^4-\overset{\overset{\displaystyle O}{\|}}{C}-OR^3$$

wherein $R^4$ is a $-(CH_2)_n-$ group or a group containing at least one double bond $-CH=CH-(CH_2)_{n-2}-$ where n is from 1 to 20 and $R^3$ is a $C_1$ to $C_6$ alkyl group.

8. The method according to claim 7 wherein $R_3$ is a $C_1$ to $C_3$ alkyl group.

9. The method according to the claim 1 wherein $R_1$ or $R_2$ is selected from the group consisting of methyl, ethyl, propyl, butyl, pentyl, hexyl, heptyl, 4-methylpentyl, 5-methylhexyl, cyclopentyl, cyclohexyl, vinyl, propenyl, butenyl, pentenyl, hexenyl, heptenyl, 3-methylbutenyl, 5-methylhexenyl, benzyl, ethylbenzene, propylbenzene, ethyl propanoate and ethyl propenoate.

10. The method according to claim 9 where $R_1$ or $R_2$ is a methyl group.

11. A method of repelling a population of insects susceptible to the venom of *Solenopsis invicta* comprising exposing to said population a composition comprising an effective amount of a trans-2,6-disubstituted piperidine compound according to the structure:

wherein $R^1$ and $R^2$ are selected from a $C_1$ to $C_{20}$ saturated or unsaturated linear, cyclic or branch-chained substituted or unsubstituted hydrocarbon group, a substituted or unsubstituted aromatic group or an ester group and salts thereof; optionally, in combination with a carrier.

12. The method according to claim 11 wherein said hydrocarbon group is an alkyl group.

13. The method according to claim 11 wherein said hydrocarbon group is an alkenyl group.

14. The method according to claim 11 wherein said alky group is a $C_2$ to $C_9$ alkyl group.

15. The method according to claim 11 wherein said hydrocarbon is a substituted or unsubstituted aromatic group.

16. The method according to claim 11 wherein said hydrocarbon is an aromatic substituted alkyl group.

17. The method according to claim 11 wherein said ester group contains a chemical structure according to the formula:

$$R^4-\overset{\overset{\displaystyle O}{\|}}{C}-OR^3$$

wherein $R^4$ is a $-(CH_2)_n-$ group or a group containing at least one double bond $-CH=CH-(CH_2)_{n-2}-$ where n is from 1 to 20 and $R^3$ is a $C_1$ to $C_6$ alkyl group.

18. The method according to claim 11 wherein $R_3$ is a $C_1$ tio $C_3$ alkyl group.

19. The method according to the claim 11 wherein $R_1$ or $R_2$ is selected from the group consisting of methyl, ethyl, propyl, butyl, pentyl, hexyl, heptyl, 4-methylpentyl, 5-methylhexyl, cyclopentyl, cyclohexyl, vinyl, propenyl, butenyl, pentenyl, hexenyl, heptenyl, 3-methylbutenyl, 5-methylhexenyl, benzyl, ethylbenzene, propylbenzene, ethyl propanoate and ethyl propenoate.

20. The method according to claim 19 where $R_1$ or $R_2$ is a methyl group.

* * * * *